(12) United States Patent
Oliver et al.

(10) Patent No.: US 9,737,322 B2
(45) Date of Patent: Aug. 22, 2017

(54) METHOD FOR RESECTION OF TUMORS AND TISSUES

(71) Applicant: MEDTRONIC-XOMED, INC., Jacksonville, FL (US)

(72) Inventors: Dana A. Oliver, Jacksonville, FL (US); Phillip J. Berman, Jacksonville, FL (US); Thoai Nguyen, Jacksonville, FL (US); Louis M. Shadeck, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 153 days.

(21) Appl. No.: 14/479,729

(22) Filed: Sep. 8, 2014

(65) Prior Publication Data
US 2016/0066943 A1   Mar. 10, 2016

(51) Int. Cl.
*A61B 17/32* (2006.01)
*A61B 17/22* (2006.01)
*A61B 17/3207* (2006.01)

(52) U.S. Cl.
CPC .... *A61B 17/32002* (2013.01); *A61B 17/3207* (2013.01); *A61B 17/320783* (2013.01); *A61B 2017/22079* (2013.01); *A61B 2017/32004* (2013.01); *A61B 2017/320024* (2013.01);
(Continued)

(58) Field of Classification Search
CPC .......... A61B 17/32002; A61B 17/3207; A61B 17/320783; A61B 2017/22079; A61B 2017/320024; A61B 2017/32004; A61B 2017/320064
See application file for complete search history.

(56) References Cited

U.S. PATENT DOCUMENTS

| 3,844,272 A | 10/1974 | Banko |
| 4,167,943 A | 9/1979 | Banko |
| 4,274,414 A | 6/1981 | Johnson et al. |

(Continued)

FOREIGN PATENT DOCUMENTS

WO   2008124650 A1   10/2008

OTHER PUBLICATIONS

International Search Report and Written Opinion for Application No. PCT/US2015/47724, mailed Dec. 21, 2015, 15 pages.
(Continued)

*Primary Examiner* — Robert Lynch
(74) *Attorney, Agent, or Firm* — Dicke, Billig & Czaja, PLLC

(57) ABSTRACT

A surgical method of removing tissue of a patient includes grasping a surgical cutting instrument. The instrument includes an outer blade including a tubular body, an end cap, and a cutting window defined by an edge on at least the end cap, and an inner blade including a cutting tip, the inner blade co-axially disposed within the outer blade, the cutting tip including a cutting edge extending toward the end cap of the outer blade, wherein the cutting tip is rotatably exposed at the cutting window. The method further includes positioning the cutting window and cutting tip to a target site, supplying fluid through an irrigation pathway to the cutting window and the target site, rotating the cutting tip of the inner blade to selectively cut the tissue, and aspirating fluid and cut tissue.

18 Claims, 15 Drawing Sheets

(52) U.S. Cl.
CPC ............. *A61B 2017/320064* (2013.01); *A61B 2217/005* (2013.01); *A61B 2217/007* (2013.01)

(56) References Cited

U.S. PATENT DOCUMENTS

| | | | |
|---|---|---|---|
| 4,598,710 A † | 7/1986 | Kleinberg | |
| 4,811,734 A | 3/1989 | McGurk-Burleson et al. | |
| 4,834,729 A * | 5/1989 | Sjostrom | A61B 17/32002 604/22 |
| 4,850,354 A | 7/1989 | McGurk-Burleson et al. | |
| RE33,258 E | 7/1990 | Onik et al. | |
| 4,983,179 A | 1/1991 | Sjostrom | |
| 4,986,827 A | 1/1991 | Akkas et al. | |
| 5,007,917 A | 4/1991 | Evans | |
| 5,275,609 A | 1/1994 | Pingleton et al. | |
| 5,376,078 A | 12/1994 | Dinger, III et al. | |
| 5,409,013 A | 4/1995 | Clement | |
| 5,437,630 A | 8/1995 | Daniel et al. | |
| 5,601,583 A | 2/1997 | Donahue et al. | |
| 5,620,447 A | 4/1997 | Smith et al. | |
| 5,643,304 A | 7/1997 | Schechter et al. | |
| 5,669,876 A | 9/1997 | Schechter et al. | |
| 5,676,012 A | 10/1997 | Ceriale | |
| 5,685,840 A | 11/1997 | Schechter et al. | |
| 5,690,660 A | 11/1997 | Kauker et al. | |
| 5,709,698 A | 1/1998 | Adams et al. | |
| 5,766,199 A | 6/1998 | Heisler et al. | |
| 5,782,795 A | 7/1998 | Bays | |
| 5,792,167 A | 8/1998 | Kablik et al. | |
| 5,863,294 A | 1/1999 | Alden | |
| 5,964,777 A | 10/1999 | Drucker | |
| 6,183,433 B1 | 2/2001 | Bays | |
| 6,217,598 B1 | 4/2001 | Berman et al. | |
| 6,419,684 B1 | 7/2002 | Heisler et al. | |
| 6,620,180 B1 | 9/2003 | Bays et al. | |
| 6,638,289 B1 | 10/2003 | Johnson et al. | |
| 7,641,667 B2 | 1/2010 | Sample | |
| 7,674,263 B2 | 3/2010 | Ryan | |
| 7,803,170 B2 | 9/2010 | Mitusina | |
| 8,070,765 B2 | 12/2011 | Oliver et al. | |
| 8,202,288 B2 | 6/2012 | Adams et al. | |
| 8,409,235 B2 | 4/2013 | Rubin | |
| 8,414,606 B2 | 4/2013 | Shadeck et al. | |
| 9,486,232 B2 | 11/2016 | Heisler et al. | |
| 2005/0159767 A1* | 7/2005 | Adams | A61B 17/32002 606/180 |
| 2006/0200123 A1 | 9/2006 | Ryan | |
| 2007/0149975 A1* | 6/2007 | Oliver | A61B 17/32002 606/79 |
| 2007/0219549 A1 | 9/2007 | Marshall et al. | |
| 2007/0282361 A1 | 12/2007 | Da Rold et al. | |
| 2008/0200941 A1* | 8/2008 | Mitusina | A61B 17/32002 606/171 |
| 2009/0270894 A1 | 10/2009 | Rubin et al. | |
| 2010/0152761 A1 | 6/2010 | Mark | |
| 2010/0191266 A1* | 7/2010 | Oliver | A61B 17/320783 606/170 |
| 2010/0298763 A1 | 11/2010 | Adams et al. | |
| 2012/0109172 A1 | 5/2012 | Schmitz et al. | |
| 2012/0157879 A1 | 6/2012 | Mark et al. | |
| 2012/0191117 A1 | 7/2012 | Palmer et al. | |
| 2013/0012972 A1 | 1/2013 | Norman et al. | |
| 2014/0303551 A1* | 10/2014 | Germain | A61B 17/22 604/30 |

OTHER PUBLICATIONS

International Search Report and Written Opinion for Application No. PCT/US2015/48015, mailed Jan. 18, 2016, 15 pages.

* cited by examiner
† cited by third party

METHOD FOR RESECTION OF TUMORS AND TISSUES

CROSS-REFERENCE TO RELATED APPLICATIONS

This Utility patent application is related to concurrently filed Utility patent application Ser. No. 14/479,720, entitled TUMOR MARGIN DEVICE and Utility patent application Ser. No. 14/479,714, entitled TUMOR DEBULKER.

BACKGROUND

The present disclosure relates to treatment of tumors on or near the brain or spine. More particularly, it relates to surgical methods useful in reducing and/or removing tumors, fibrous tissues, spinal discs, and ligaments.

Neurosurgery is the treatment of choice for accessible brain tumors. The goal of surgery is to remove as much tumor tissue as possible. The most commonly performed surgery for removal of a brain tumor is a craniotomy. In general, the neurosurgeon makes an incision into the scalp, cranium, dura, meninges, and cortex to expose an area of brain over the tumor. Location and removal of the tumor then takes place. In this regard, a variety of surgical instruments, such as a cavitational ultrasonic surgical aspirator (CUSA) or a surgical laser knife, are commonly used.

The delicate tissues associated with the human brain anatomy give rise to several concerns when using a CUSA, laser knife, or other brain surgery instrument. By way of reference, the brain is covered by three membranes or meninges that in turn are surrounded by the skull. The three layers of meninges are the dura mater (immediately beneath the skull), the arachnoid, and the pia mater. Spinal fluid flows in the space between the arachnoid and the pia mater membranes, known as the subarachnoid space. These meninges are thin and delicate, with the pia mater carrying or maintaining the many blood vessels associated with the brain. Due to the friable nature of especially the pia mater, neurosurgeons must exercise great care when attempting to surgically remove a brain tumor; unintended damage to the pia mater can diminish the blood supply to the brain. Unnecessary injury to other healthy structures, such as the arachnoid or brain tissue (e.g., cerebral cortex) can also lead to patient impairment. With this in mind, CUSA instruments deliver ultrasonic action to remove tissue and bone. The surgeon attempts to place the ultrasonic cutting tip against tissue to be destroyed. However, high frequency cutting may also occur and damage tissue surrounding the targeted tumor when touched by the instrument's shaft. Further, due to the relatively large size of the CUSA handpiece, it may be difficult to visually confirm placement of the ultrasonic shaft/tip. Similarly, use of a laser knife may give rise to unintended tissue damage with thermal insult or thermal collateral of surrounding viable tissue due to local heat in and around the incision line. Additionally, ultrasonic devices can cause a spray of cancerous matter during treatment.

Further, typical oscillating microdebrider blades cause jerking of the blade as the blade rotation changes direction. These microdebrider blades often tear off chunks of tissue and do not provide clean, straight cuts.

In light of the above, a need exists for surgical systems and methods for reducing or removing brain tumors while minimizing the likelihood of normal tissue damage.

SUMMARY

Some aspects in accordance with principles of the present disclosure relate to a surgical method of removing tissue of a patient including grasping a surgical cutting instrument. The instrument includes an outer blade including a tubular body, an end cap, and a cutting window defined by an edge on at least the end cap, and an inner blade including a cutting tip, the inner blade co-axially disposed within the outer blade, the cutting tip including a cutting edge extending toward the end cap of the outer blade, wherein the cutting tip is rotatably exposed at the cutting window. The method further including positioning the cutting window and cutting tip to a target site, supplying fluid through an irrigation pathway to the cutting window and the target site, rotating the cutting tip of the inner blade to selectively cut the tissue, and aspirating fluid and cut tissue.

Other aspects in accordance with principles of the present disclosure relate to a surgical method of removing tissue of a patient. The method includes operating a surgical system including a surgical instrument. The surgical instrument includes an outer blade including a planar distal end cap and a cutting window at least partially formed in the distal end cap, an inner blade including a cutting tip rotatably received within the outer blade, the cutting tip selectively exposed at the cutting window, an aspiration pathway defined by the inner blade, and an irrigation pathway defined between an outer surface of the inner blade and an inner surface of the outer blade. The irrigation and aspiration pathways terminate at the cutting window. The method also includes delivering the surgical instrument to a target site, positioning the cutting window and cutting tip at the target site, supplying fluid through the irrigation pathway to the cutting tip, selectively rotating the inner blade in a single direction, emulsifying the tissue selectively exposed to the cutting tip, and selectively aspirating fluid and emulsified tissue through the cutting window and aspiration pathway.

Other aspects in accordance with principles of the present disclosure relate to a surgical method of removing tissue of a patient including operating a surgical cutting system. The surgical cutting system includes a surgical cutting instrument. The surgical cutting instrument includes an outer blade, an inner blade coaxially received within the outer tubular member, a distal end of the inner blade and the outer blade forming a cutter including at least one cutting window on outer tubular member and a cutting tip rotatable with the inner blade, and a handpiece including a manual aspiration control, the handpiece fixedly maintaining a proximal end of the outer blade and rotatably maintaining a proximal end of the inner blade. The method includes fluidly coupling an irrigation source to a lumen of the inner blade and fluidly coupling a negative pressure source to the outer blade. The method also includes selectively controlling the irrigation source, and the negative pressure source with an electrical console. The method includes delivering the cutting window and cutting tip to a target site, supplying fluid through an irrigation pathway at least partially disposed between the inner blade and the outer blade to the cutting window, selectively controlling the rotation of the inner blade via the electrical console to cut tissue, rotating the inner blade to selectively expose the cutting tip at the cutting window, emulsifying tissue exposed to the cutting tip, and aspirating the emulsified tissue and fluid via the negative pressure source

DETAILED DESCRIPTION

In the following detailed description, reference is made to the accompanying drawings which form a part hereof, and in which are shown by way of illustration specific examples in which the disclosure can be practiced. It is to be understood that other examples may be utilized and structural or logical changes can be made without departing from the scope of the present disclosure. The following detailed description, therefore, is not to be taken in a limiting sense, and the scope of the present disclosure is defined by the appended claims. It is to be understood that features of the various examples described herein can be combined, in part or whole, with each other, unless specifically noted otherwise.

Surgical methods embodying principles of the present disclosure can be employed in various types of surgery including, but not limited to, neurosurgery or spinal surgery on the dura or spinal column. Surgical methods according to aspects of the present disclosure can be used to resect a wide range of tumors, from soft tumors to very fibrous tumors, including very fibrous meningioma. Fibrous tissue often contains high collagen content and is a form of connective tissue. In terms of tumors arising from high collagen content tissues, the tumors may replicate the properties of the tissues and therefore present a challenge to resection.

Figure 1:
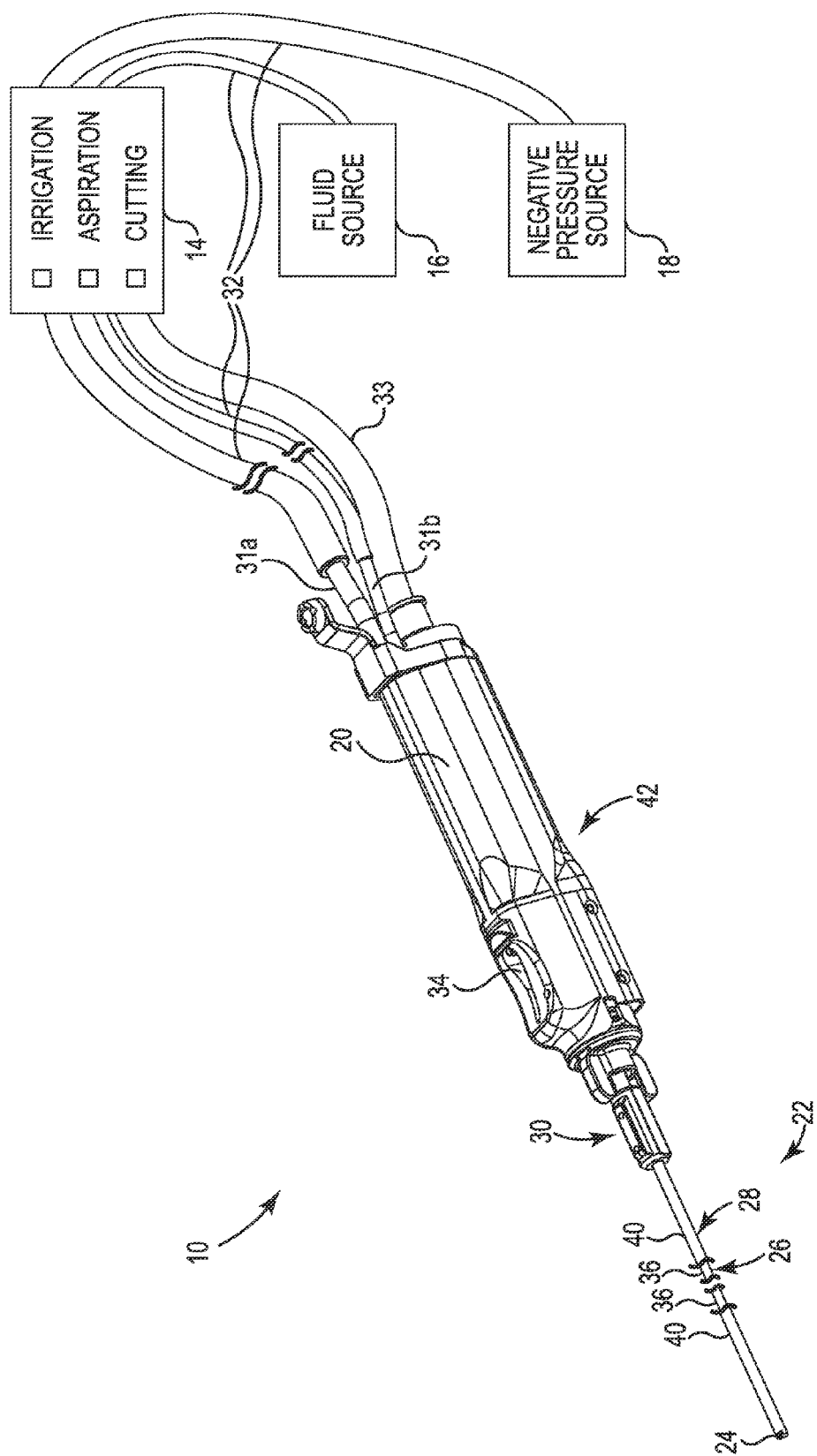
FIG. 1 is a perspective view of a surgical system including a cutting instrument for surgically reducing or removing a tumor or fibrous tissue in accordance with principles of the present disclosure.

A surgical system 10 in accordance with aspects of the present disclosure for use in the resection of various tumors and tissues in the central nervous system (CNS) including intracranial tumors and fibrous spinal tissues as part of surgery is shown in FIG. 1. The system 10 includes a surgical cutting instrument 12, an Integrated Power Console (IPC) 14, a fluid source 16, and a negative pressure source 18. Details on the various components are provided below. In general terms, however, the surgical cutting instrument 12 includes a handpiece 20 and a cutting implement 22 extending distally from the handpiece 20 terminating at a cutter 24 having a cutting tip and a cutting window, as discussed in more detail below. The cutting implement 22 includes an inner blade assembly 26, an outer blade assembly 28, and a window orientation assembly 30. The fluid source 16 and the negative pressure source 18 are fluidly connected to the cutting implement 22 via fluid pathways 31a, 31b, respectively, extending through the handpiece 20.

The IPC 14 provides automated electromechanical control for the system 10. A tubing set 32 including an irrigation tube and a suction tube are fluidly connected to the handpiece 20 and loaded into the IPC 14. The IPC 14 is electrically connected to a motor (not shown) maintained by the handpiece 20 via a power and control cable 33. The IPC 14 enables selective rotational control of the cutting implement 22 and fluid control over the fluid source 16. Additional control of the negative pressure supplied to the cutting implement 22 is adjustable by an aspiration control hole 34 (referenced generally) on the handpiece 20 as discussed further below.

The handpiece 20 includes a housing that contains a motor (not shown) for driving the rotational movement of the inner blade assembly 26. The handpiece 20 receives proximal ends of the inner and outer blade assemblies 26, 28 for fluidly connecting internal irrigation and aspiration paths (each not shown) with an fluid pathways 31a, 31b, respectively, assembled to the handpiece 20. Regardless, the irrigation path 31b is formed within the handpiece 20 extending through the outer blade assembly 28 to cutting window. Similarly, the aspiration pathway 31a formed within the handpiece 20 fluidly extends through the inner blade assembly 26 to the cutting tip and is in fluid communication with the negative pressure source 18 for applying a negative pressure, or vacuum, to the aspiration path, and thus to the inner blade assembly 26. The negative pressure source 18 can be a direct wall suction source or an accessory vacuum pump, for example. Various aspects of the cutting tip and cutting window are discussed in more detail below. Additional control of the negative pressure supplied to the cutting tip is provided by the aspiration control hole 34 on the handpiece 20.

Figure 2:
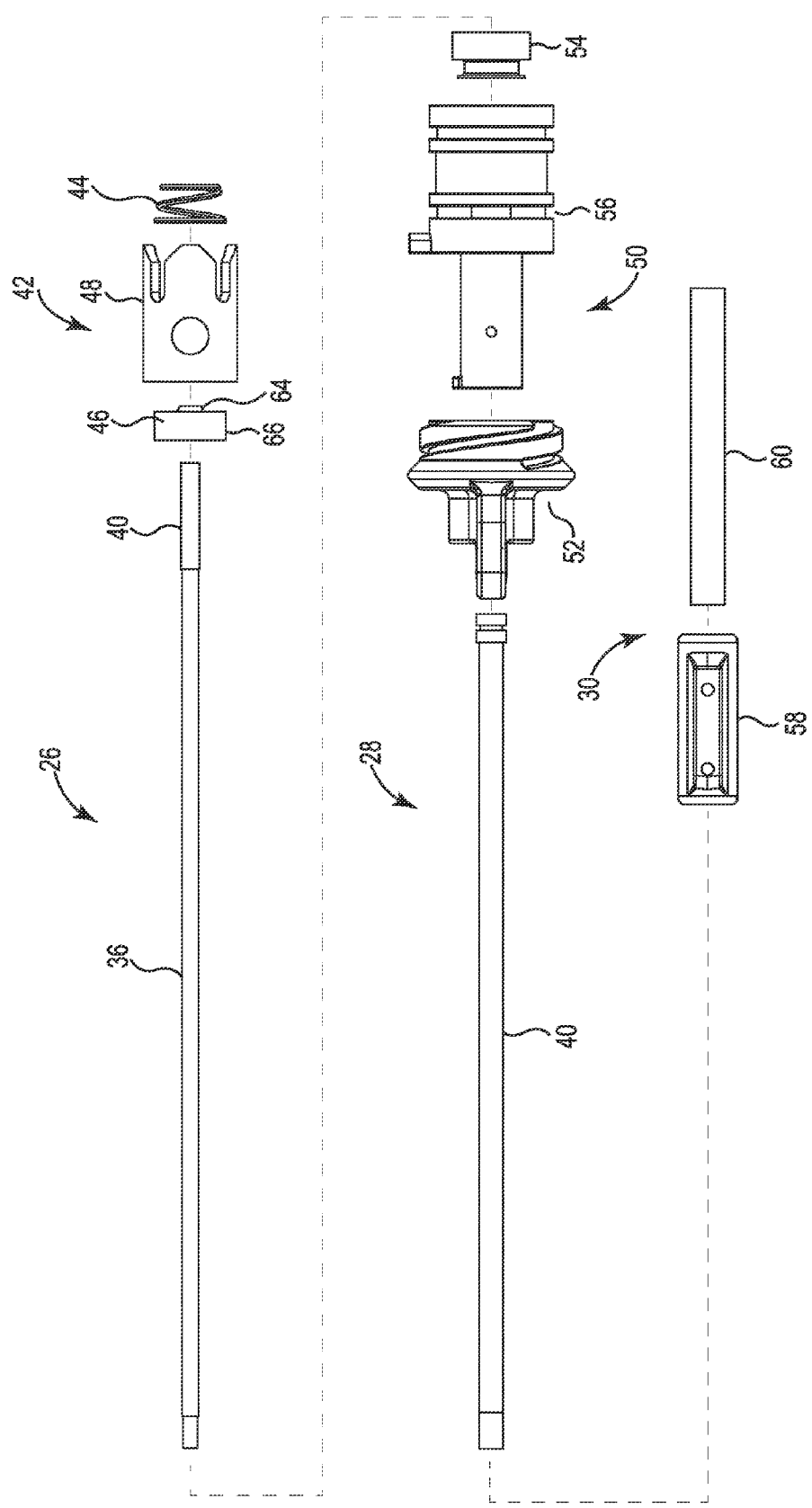
FIG. 2 is an exploded view of the cutting implement of FIG. 1.

With the above general construction of the surgical system 10 in mind, features associated with the cutting implement 22 in accordance with aspects of the present disclosure are shown in greater detail in FIG. 2. The cutting implement 22 includes the inner blade assembly 26 having an inner blade 36 and the outer blade assembly 28 having an outer blade 40. In general terms and with additional reference to FIGS. 3A and 3B, the inner blade 36 is rotatably received within the outer blade 40, with the other components of the assemblies 26, 28 effectuating connection to the handpiece 20. Regardless, the outer and inner blades 36, 40 extend distally from the handpiece 20 and combine to form the cutting implement 22 and cutter 24 as described below. The cutting implement 22, and in particular the blades 36, 40, can have a linear or straight configuration, as shown in FIG. 2, or can alternatively have a curved or bent construction. In the case of a curved or bent construction, the location and degree of curvature or bend is predetermined to suitably accommodate the desired surgical procedure.

The inner blade 36 defines an aspiration pathway through an interior of the cutting implement 22 to the cutter 24. The inner blade 36 has an inner surface that defines a lumen. The inner blade 36 defines a lumen between an open proximal end and a distal end, the distal end having an opening therein communicating with the pathway/lumen and forming a suction inlet through which cut bodily tissue can be aspirated. The inner surface of the inner blade 36 generally defines a uniform diameter and is generally uniformly smooth and free from burs. The inner blade 36 has a length such that the aspiration pathway may extend continuously through a hub assembly of both the inner blade 36 and the outer blade 40. In particular, the inner blade 36 is coaxially disposed within the outer blade 40 such that a distal end of the outer blade 40 is proximal to a distal end of the inner blade 36. The inner blade 36 has a distal portion, an intermediate portion, and a proximal portion. In one embodiment, the proximal portion has a slightly larger outer diameter than either the distal portion or the intermediate portion. In one embodiment, at least a portion of the proximal end of the inner blade 36 is textured to include a raised fine diamond knurl (not shown). Regardless, the inner blade 36 is an elongated tubular body and terminates at the distal cutting tip is formed in the distal portion.

The inner blade assembly 26 includes the inner blade 36 as well as an inner hub assembly 42. As described below, the inner hub assembly 42 maintains the inner blade 36 and facilitates connection of the inner blade assembly 26 to a motor (not shown). The inner hub assembly 42 includes a spring 44, an inner hub 46 and a drive hub 48. The inner hub 46 and the drive hub 48 can assume a variety of forms. The inner hub 46 is adhesively, thermally, or otherwise bonded to the drive hub 48. The inner blade 36 extends within the inner hub 46 and is welded or otherwise bonded to the inner hub 46.

With continued reference also to FIG. 2, the outer blade 40 is an elongated tubular body defining a distal end, a proximal end, and a central lumen extending between the proximal end and the distal end. The central lumen generally defines a uniform diameter and is generally uniformly smooth. With additional reference to FIGS. 3A and 3B, the inner blade 36 is maintained within the central lumen of the outer blade 40 such that an outer surface of the inner blade 36 and an inner surface of the outer blade 40 define an irrigation pathway to the cutter 24 when assembled. The central lumen of the outer blade 40 is sized to accommodate the inner blade 36 coaxially within and maintain the irrigation pathway between walls of the inner blade 36 and outer blade 40. In one embodiment, the proximal end of the outer blade 40 includes a thickened wall (not shown) that reduces or removes vibration at the cutter 24 caused by the rotation of the inner blade 36 and the cutter 24 during operation.

In addition to the outer blade 40, the outer blade assembly 28 includes an outer hub assembly 50 having a fastener 52, a dynamic seal 54, and an outer hub 56. The outer blade 40 extends distally from within the outer hub 56. The fastener 52 removably secures the hub assemblies 42, 50 within the handpiece 20 (not shown). The outer hub assembly 50 can assume a wide variety of forms.

The outer blade 40 is assembled to the outer hub assembly 50 and the inner blade 36 is assembled to the inner hub assembly 42. The inner blade 36 is coaxially received within the outer blade 40 and the outer hub assembly 50. The assembled hubs are coaxially received within the handpiece 20 (not shown), with the outer blade 40 and inner blade 36 extending distal the hubs 46, 56 to terminate at the cutter 24. The inner hub assembly 42 and the outer hub assembly 50 cooperate to facilitate the rotational relationship of the inner blade 36 and the outer blade 40 by the handpiece 20 that supports both the inner blade assembly 26 and the outer blade assembly 28. Rotation of the inner blade 36 is translated to the cutter 24 to effect debriding of the target tissue at the treatment site, as described in greater detail below.

In this regards, the dynamic seal 54 can be provided to effectuate a fluid-tight seal between the inner blade 36 and the outer blade 40. The dynamic seal 54 can be maintained within a bore 57 at the distal end of the outer hub 56 to seal around the inner blade 36 extending through the outer hub 56. The dynamic seal 54 is configured to fluidly seal around the proximal portion of the inner blade 36. With this construction, an irrigation liquid (not shown) to the outer blade 40 can be delivered to the lumen of the outer blade 40 via a sealed pathway. The inner blade 36 extends through the dynamic seal 54 to fluidly seal within the inner hub 46 of the inner hub assembly 42. With this construction, aspirated liquids and solids (not shown) can be delivered from the cutter 24 through the lumen of the inner blade 36 via a sealed pathway. Other constructions capable of effectuating flow of irrigation liquid to the outer blade 40 and aspiration to the inner blade 36 are also envisioned.

The window orientation assembly 30 includes a window orientation hub 58 and a tubular shaft 60. The inner diameter of the tubular shaft 60 is sized appropriately to accommodate the outer blade 40. In one embodiment, the proximal end of the tubular shaft 60 has an inner diameter larger than the remainder of the tubular shaft 60 in order to accommodate radial rings at the proximal region of the outer blade 40 (see, e.g., FIG. 3B). Features associated with one embodiment of the window orientation assembly 30 in accordance with aspects of the present disclosure are shown in greater detail in FIG. 3B.

Figure 3A:
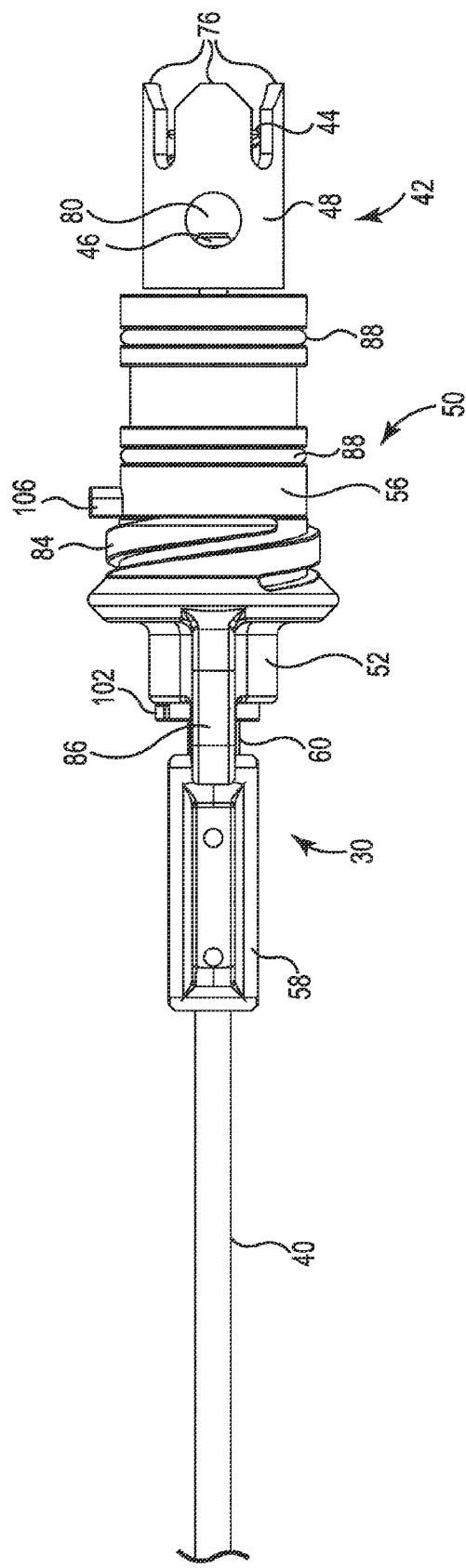
FIGS. 3A and 3B are partial side and cross-sectional views of the cutting implement of FIG. 1.
Figure 3B:
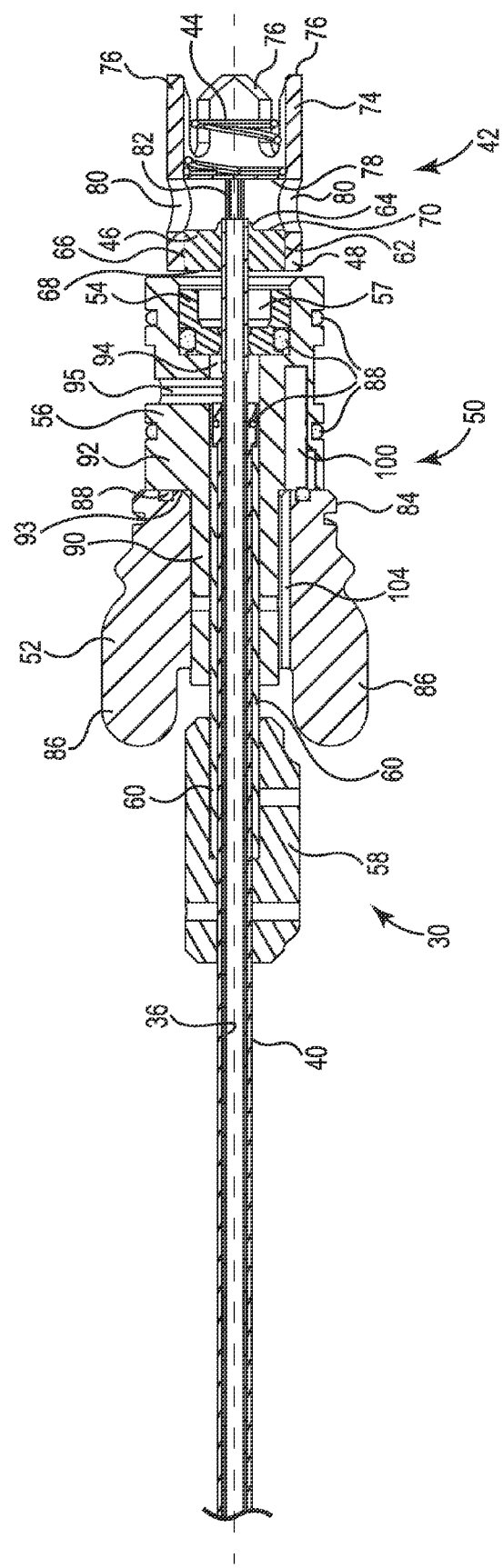

More particularly, with reference to FIGS. 3A and 3B, the inner blade 36 is assembled to the inner hub 46 that is assembled to the drive hub 48 of the inner hub assembly 42. The window orientation assembly 30 is assembled to the outer blade 28 that is assembled to the outer hub assembly 50. The inner blade assembly 26 is assembled with the outer blade assembly 28 and the hub assemblies 42, 50 are coaxially received within the handpiece 20 (see, e.g., FIG. 1), with the outer blade 40 and inner blade 36 extending distal the hub assemblies 42, 50. The inner hub assembly 42 and the outer hub assembly 50 cooperate to facilitate the rotational relationship of the inner blade 36 and the outer blade 40 by the handpiece 20. Rotation of the inner blade 36 within the handpiece 20 is translated to the cutting tip to effect selectively removing the target tissue at the treatment site, as described in greater detail below. With this construction, aspirated liquids and solids (not shown) can be delivered from the cutting tip through the lumen of the inner blade 36 via a sealed pathway. Other constructions capable of effectuating flow of irrigation liquid to the outer blade 40 and aspiration through the inner blade 36 are also envisioned.

The inner blade 36 is insertable into and connectable to the inner hub 46 to provide a fluid connection of the interior of the inner blade 36 with the central port 62 of the inner hub 46 along the longitudinal axis. The inner hub 46 is generally annular and includes a central port 62 and radial side walls 66 extending between a first surface 68 and an opposing second surface 70. The central port 62 terminates in a tapered lip 64. The central port 62 is sized and shaped to accommodate the inner blade 36. The tapered lip 64 extends from the either the first or second surface 68, 70 to effectuate weld joint development between the inner hub 46 and the inner blade 36 (see, e.g., FIG. 3B).

The drive hub 48 of the inner hub assembly 42 includes perimeter walls 74 terminating at one end in prongs 76. The prongs 76 are configured to facilitate connection with the motor housed in the handpiece 20. The drive hub 48 has an open proximal end and an open distal end. In one embodiment, a stop 78 extends generally perpendicular to the perimeter walls 74 between the proximal end and the distal end. The stop 78 is formed between side ports 80 and the prongs 76 along the longitudinal axis. The stop 78 provides a distal stop for the spring 44. The distal end of the drive hub 48 is configured to receive the inner hub 46 and in some cases terminates at a planar surface. The perimeter walls 74 define a cylindrical body. Side ports 80 are formed in the perimeter walls 74. In one embodiment, the perimeter walls 74 include two diametrically opposed side ports 80. The side ports 80 of the drive hub 48 are configured to fluidly connect with the central port 62 of the inner hub 46 and the lumen of the inner blade 36.

A length of the radial side walls 66 along the longitudinal axis between the first surface 68 and the second opposing surface 70 is such that it does not infer with fluid flow of side ports 80 of the drive hub 48. The radial side walls 66 are configured for insertion within the perimeter walls 74 of the drive hub 48. In one embodiment, the rim 72 extends fully within the drive hub 48. The radial side walls 66 fit tightly within the drive hub 48 and form a fluid tight seal against the perimeter walls 74. In one embodiment, the drive hub 48 includes inner hub stops 82 that extend from the stop 78 to a predetermined distance along the inner surface of the perimeter walls 74. The predetermined distance is a distance suitable to allow the inner hub 46 to be inserted into the drive hub 48. As assembled, the inserted inner hub 46 is clear of, and does not block, fluid communication of the side ports 80. The inner hub stops 82 extend across the diameter of the side ports 80 on the inner surface of the drive hub 48 radially adjacent to the side ports 80. The stop 78 extends across a diameter of the drive hub 48 proximal to the side ports 80 opposing the inner hub 46. In other words, when assembled, the stop 78 and the drive hub 48 are disposed on opposite sides of the side ports 80.

The fastener 52 includes an open core, or lumen, extending longitudinally through the fastener 52 and open at both proximal and distal ends. The core is sized and shaped for a distal portion of the outer hub 56 to extend through, as discussed further below. The fastener 52 includes threads 84 on an exterior surface to removably secure the outer hub assembly 50 within the handpiece 20 (i.e., threads 84 are mate-able with threads in the handpiece 20, not shown). The fastener 52 includes winged tabs 86 extending distally away from the threads 84 as well as radially outward. The winged tabs 86 are configured for ease of handling and turning the threads 84 of the fastener 50 to engage or disengage the cutting implement 22 to or from the handpiece 20 (see FIG. 1). Other engagement and disengagement mechanisms are also acceptable. In one embodiment, two winged tabs 86 are included and are disposed on opposing sides of the fastener 52, although other quantities and configurations of winged tabs 86 can also be suitable. In one embodiment, threads 84 are provided to allow the fastener 52 to be turned 180° when securing within the handpiece 20. Sufficient threads 84 are included to prevent the fastener 52 from inadvertently disengaging from the handpiece 20 when the surgical cutting instrument is in use. In any regard, suitable threads 84 are provided to secure the outer hub assembly 50, and the cutting implement 22, to the handpiece 20 until a user rotates the fastener 52 by rotationally pushing against the winged tabs 86 to disengage the threads 84 from the handpiece 20. In one embodiment, a notch is included at the proximal end and an o-ring 88 is insertable into the notch. The o-ring 88 is disposed the outer hub 56 when assembled and can absorb some of the vibrations of the cutting implement 22 during operation.

The outer hub 56 includes a neck 90 and a base 92. A radial shoulder 93 is defined between the neck 90 and the base 92 and radially extends from an outer diameter of the neck 90 to an outer diameter of the base 92. The neck 90 is sized and configured to extend within and through the fastener 52. A passageway 94 extends through the neck 90 and the base 92. An irrigation port 95 extends from an exterior surface of the outer hub 56 and fluidly connects with the passageway 94. In one embodiment, the passageway 94 extends along the longitudinal axis and the irrigation port 95 extends perpendicularly to the exterior surface of the outer hub 56. In accordance with aspects of the disclosure, the irrigation port 95 is disposed within the handpiece 20 to fluidly connect to the fluid pathway 31a when assembled to the handpiece 20.

With additional reference to FIG. 3B, the outer blade 40 extends within the passageway 94 and terminates distal to the irrigation port 95 such that the irrigation port 95 freely communicates with the lumen of the outer blade 40. The outer blade 40 is adhesively attached within the outer hub 56. At least one glue weep port 96 extends at an angle to, and in some cases perpendicular, to the longitudinal axis extending along a length of the passageway 94. The at least one adhesive weep port 96 directly and fluidly connects to the passageway 94 and is also fluidly open at an exterior surface of the outer hub 56. Adhesive (not shown), when used to adhere the outer blade 40 within the passageway 94 of the outer hub 56, is inserted in the distal end after or with insertion of the outer blade 40 and excess adhesive can exit the neck 90 at least one adhesive weep port 96 during assembly.

With continued reference to FIG. 3B, the inner blade 36 extends beyond the proximal end of the outer blade 40 and through the dynamic seal 54 disposed in the bore 57 at the proximal end portion of the outer hub 56 to connect with the inner hub assembly 42. The dynamic seal 54 fluidly seals around the inner blade 36. In addition, as described in greater detail below, the outer surface of the outer hub 56 is adapted to receive seal rings 88 (e.g., o-rings) on either side of an irrigation port 95 to effectuate a fluid-tight seal between the outer hub 56 and the handpiece 20 (not shown). In some embodiments, the dynamic seal 54 and the seal rings 88 are a polytetrafluoroethylene (PTFE) material such as Teflon®, although other suitable materials are also acceptable.

In one embodiment, the outer hub 56 includes an identification port 100. The identification port 100 is configured to accept a radio-frequency identification (RFID). The RFID includes data to identify the size and blade type, for example, of the cutting implement 22 that is transferred to the IPC 14 when the cutting implement 22 is assembled with the handpiece 20. The IPC 14, upon receiving information from the RFID, can supply power to operate the cutting implement 22 at a suitable speed as well as fluid flow suitable for the specific cutting implement 22. Other cutting implement identification systems, such as magnetic hall sensors, for example, are also acceptable.

The outer hub 56 can include a protrusion 102 at the distal end of the neck 90. The protrusion 102 is configured to align with an alignment slot 104 in the fastener 52. The protrusion 102, when rotated and disposed within alignment slot 104, couples the fastener 52 and the outer hub 56 together. Additionally, a tab 106 disposed on the base 92 extends outwardly and is aligned radially with the protrusion 102 on the neck 90. The tab 106 is configured to slideably mate within a slot in a collar of the handpiece 20 (not shown). When assembled, the tab 106 prevents the cutting implement 22 from rotating when in use and provides a reference point to the cutter 24 orientation.

Moving now to the distal end of the cutting implement, various constructions of cutters in accordance with principles of the present disclosure are shown in greater detail in FIGS. 4A-13B. Aspects of the system 10 and surgical cutting instrument 12 described above are applicable to the embodiments described further below. Regardless of the exact form, the surgical cutting instrument 12 includes a cutter having a cutting tip and cutting window useful in performing various tumors and tissues in the central nervous system (CNS), for example, including those on or near the brain or spine.

With particular reference to embodiments illustrated in FIGS. 6A-6B and 7A-7B, cutters 124, 124' of cutting implements 122, 122' are useful for debulking or reducing a large tissue volume such as a cyst or tumor. More particularly, the cutter 124 is useful in reducing and removing tumors and fibrous tissues. It is often desirable to remove the center or bulk of the target tissue as quickly as possible.

Figure 4A:
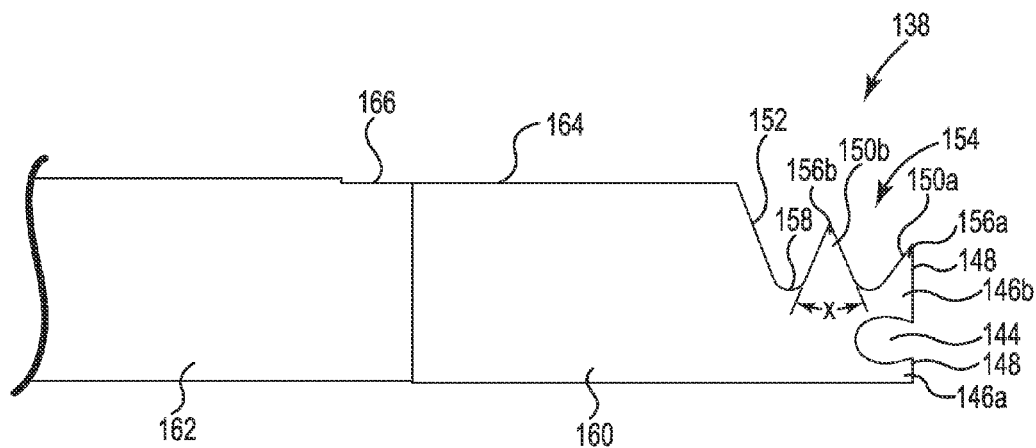
FIGS. 4A and 4B are enlarged side and top views of a distal portion of an inner blade of the cutting implement of FIG. 2 according to one embodiment.
Figure 4B:
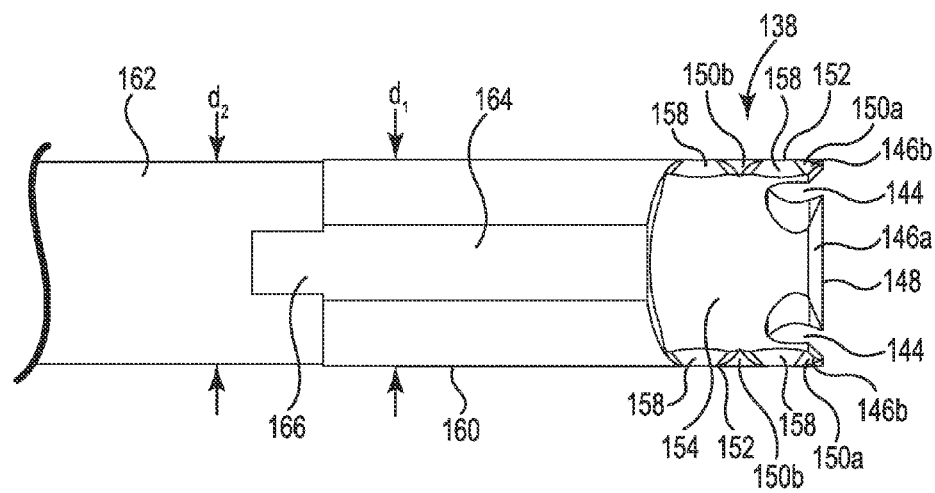
Figure 5A:
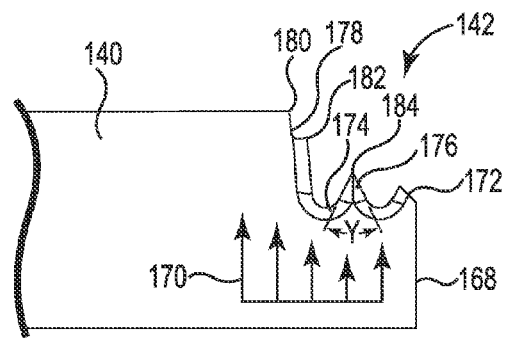
FIG. 5A is an enlarged side view of a distal end of an outer blade of the cutting implement of FIG. 2 according to one embodiment.
Figure 5B:
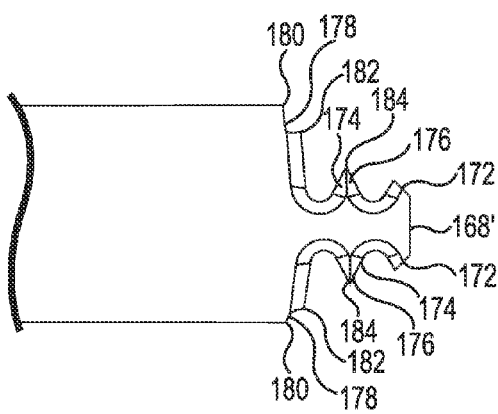
FIG. 5B is an enlarged side view of a distal end of an outer blade of a cutting implement in accordance with principles of the present disclosure.
Figure 5C:
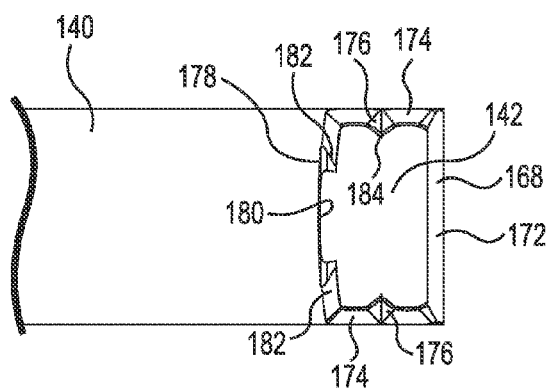
FIG. 5C is an enlarged top view of a distal end of an outer blade of a cutting implement of FIG. 5A in accordance with principles of the present disclosure.

To this end, FIGS. 4A and 4B provide enlarged side and top views of the distal portion of the inner blade 136 including the cutting tip 138, whereas FIGS. 5A through 5C illustrate embodiments of the distal region of the outer blade 140 including the cutting window 142. Upon final assembly, as best shown in FIGS. 6A and 6B or 7A and 7B, the cutting tip 138 is positioned at the cutting window(s) 142 with the two components begin rotatable relative to one another as discussed above.

The cutting tip 138 includes surfaces or edges for engaging tissue via the cutting window 142 in the distal end of the outer blade 140. The edges of the cutting tip 138 are beveled inwardly to form sharpened cutting edges such that the edge surface are beveled, or angled, toward the interior of the inner blade 136. As the inner blade 136 is rotatably driven at its proximal end, for example by the motorized handpiece 20, the surface or edge of the inner blade 136 will cooperate with the cutting window 142 in the outer blade 140 to shear, cut, or shave the tissue. In general terms, the inner geometry of the cutting tip 138 is designed to impale the tissue as the cutting tip 138 is rotated and provides both end cutting and side cutting via cylindrical geometry. As discussed further below, peripheral edges of the cutting tip 138 opening formed at cutting end of the inner blade 136 are positioned adjacent cutting window 142 such that the cutting edges of the cutting tip 138 can engage bodily tissue through the cutting window 142 and pull the tissue against the edges defining the cutting window 142 to shear the tissue.

With reference to FIGS. 4A and 4B, the cutting tip 138 includes a castellated end having notches 144 that extend between castellations 146a, 146b. In general terms, the castellations 146a, 146b form the distal end cutting surface of the inner blade 136. In one embodiment, a center castellation 146a and opposing side castellations 146b are included with U-shaped notches 144 formed in between the center castellation 146a and each of the side castellations 146b. The distal most end of the cutting tip 138 is defined by end edges 148 formed at a distal end of the castellations 146a, 146b. The end edges 148 are radially planar in a plane perpendicular to the longitudinal axis. The end edges 148 are beveled in a longitudinally inward direction to form a sharpened cutting edge. In one embodiment, the end edges 148 are beveled at a 450 angle.

Teeth 150 on opposing radial side edges 152 of a central opening 154 of the cutting tip 138. The teeth 150 are oriented in opposing pairs that are longitudinally aligned to extend toward each other across the central opening 154 of the cutting tip 138 and generally perpendicular to end edges 148 and the castellations 146a, 146b. Edge surfaces of the teeth 150 are beveled, or angled, towards the interior of the inner blade 136. Teeth 150a are formed on the opposing side castellations 146b such that tips 156a are aligned with the end edges 148 and the teeth 150a terminate distally at the end edges 148. At least one pair of teeth 150b is included along the side edges 152 of the central opening 154. The teeth 150a, 150b can have different heights. Valleys 158 are formed between tips 156a and 156b of teeth 150a, 150b. The teeth 150b are formed to have an angle "X".

As discussed above, the first outer diameter $d_1$ of distal portion 160 is slightly larger, or greater, than the second outer diameter $d_2$ of the main portion 162. For example, in one embodiment, the outer diameter $d_1$ of the distal portion 160 is 0.1452" to 0.1457" and the outer diameter $d_2$ of the main portion 162 is 0.142+/−0.001." In order maintain irrigation flow between the inner blade 136 and the outer blade 140, the irrigation channel 164 is formed along the distal portion 160 of the inner blade 136. In one embodiment, the irrigation channel 164 is a portion of the outer surface that is planar and is recessed to extend within the thickness of the inner blade between the inside surface and the outside surface. The irrigation channel 164 is centered between the radial side edges 152 to be fluidly open at the central opening 154 of the cutting tip 138. The irrigation channel 164 extends from the central opening 154 of the cutting tip 138, along the distal portion 160, to the main portion 162 of the inner blade 136. The irrigation channel 164 includes a transition section 166 on the main portion 162 adjacent to the distal portion 160. In one embodiment, the distal portion 160 has a length of 0.35" and the irrigation channel 164 has a length of 0.40".

With reference to FIGS. 5A through 5C, the cutting window 142 is formed at the distal end of the outer blade 140 is defined by shearing edges on the tubular sides and an end cap 168 of the outer blade 140. The end cap 168 can be shaped as a segment or a circular zone, for example, at the distal end of the tubular body of the outer blade 140. In this manner, both end cutting and side cutting are provided. The geometry of the cutting window 142 is configured to avoid clogging. For example, the cutting window 142 can have a length equivalent to the inner diameter of the inner blade 136 in order to avoid cutting off pieces of tissue large enough to clog the inner blade 136 and disrupt cutting. The distal end of the outer surface of the outer blade 140 can include markings 170 to visually indicate a depth of the cutting tip 138, and thus the cut, with respect to the tissue. For example, the markings 170 could be placed to indicate a cutting depth of one centimeter, two centimeters, etc. with lines and/or numbers.

In one embodiment, the end cap 168 is planar and the outer blade 140 is cylindrical rather than hemispherical at the distal end. The planar end cap 168 is perpendicular to cylindrical side walls of the outer blade 140. Alternatively, the end cap 168 can be formed as an inverted cone with a center of the inverted cone extending slightly into the interior of the outer blade 140. Regardless, the end cap 168 is joined to the tubular sides of the outer blade 140 to have a squared off interior surfaces along the perimeter. In other words, the interior corners of the distal end of the outer blade 140 at the intersection of the end cap 168 and the tubular side walls of the outer blade 140 are 90° corners. The squared off surfaces expose a maximum surface area to the cutting end edges 114 of the castellations 146a, 146b. Due to the increased cutting surface area, cutting of the tissue occurs more quickly as compared to that of a hemispherical end cutter or a cavitational ultrasonic surgical aspirator (CUSA). For example, in accordance with aspects of the present disclosure, in testing, the cutting implement 122 can resect a chicken breast at 6.78 grams/minute compared to a hemispherical end cutter resection of 2.1 grams/minute and a CUSA at 3.84 grams/minute. As an additional example, during testing the cutting implement 122 in accordance with aspects of the present disclosure can resect a chicken gizzard at 1.88 grams/minute as compared to 1.42 grams/minute with a hemispherical end cutter and 0.82 grams/minute with a CUSA.

The cutting window 142 is defined by outwardly beveled edges. An end window edge 172 is formed on the end cap 168 to form an open semi-circular shape at the distal end of the cutting implement 122. In one embodiment, the end window edge 172 is positioned such that the resulting opening is less than half of the end cap 168. In one embodiment, the end window edge 172 is linear. Side window edges 174 extend from the end window edge 172 along the tubular sides of the outer blade 140. The side window edges 174 are serrated to include window teeth 176. The window teeth 176 are disposed on opposing radial sides of the cutting window 142. Similar to the teeth 150 on the inner blade 136, the window teeth 176 are oriented in opposing pairs that are longitudinally aligned to extend toward each other across the cutting window 142 and extend generally perpendicular to the end cap 168. Edge surfaces of the window teeth 176 are beveled, or angled, towards the exterior of the outer blade 140. A suitable quantity of window teeth 176 are included on the outer blade 140 to correspond with, and interact with, the quantity of teeth 150 on the inner blade 136. In one embodiment, a single pair of window teeth 176 and a single pair of teeth 150b are provided. An angle "Y" formed by the sides of the window teeth 176 complements the angle "X" of the teeth 150b of the inner blade 136. For example, when the angle "Y" of the window teeth is 69° and the angle "X" of the teeth 150b is 59°.

As illustrated in FIG. 5C, the cutting window 142 can be generally rectangular as viewed from the top. A top window edge 178 extends between the side window edges 174 opposite the end window edge 172 to form the cutting window 142. The top window edge 178 includes a center recess 180 and opposing protrusions 182 to form additional shearing surfaces. Unlike the end and side window edges 172, 174, the top window edge 178 extends perpendicularly from the outside surface to the inside surface and is not beveled along the center recess 180.

As illustrated in FIG. 5B, an outer blade 140' can include cutting windows 142 on opposing sides of the outer blade 140'. In one embodiment, two cutting windows 142 are effectively formed on opposing sides of the outer blade 140'. An end cap 168' is formed between the cutting windows 142 as a band, or strip, extending across the end of the outer blade 140' and separating the cutting windows 142 from each other. Aspects of each of the cutting windows 142 of the outer blade 140' are as described above with respect to the cutting window 142 of the outer blade 140.

Figure 6A:
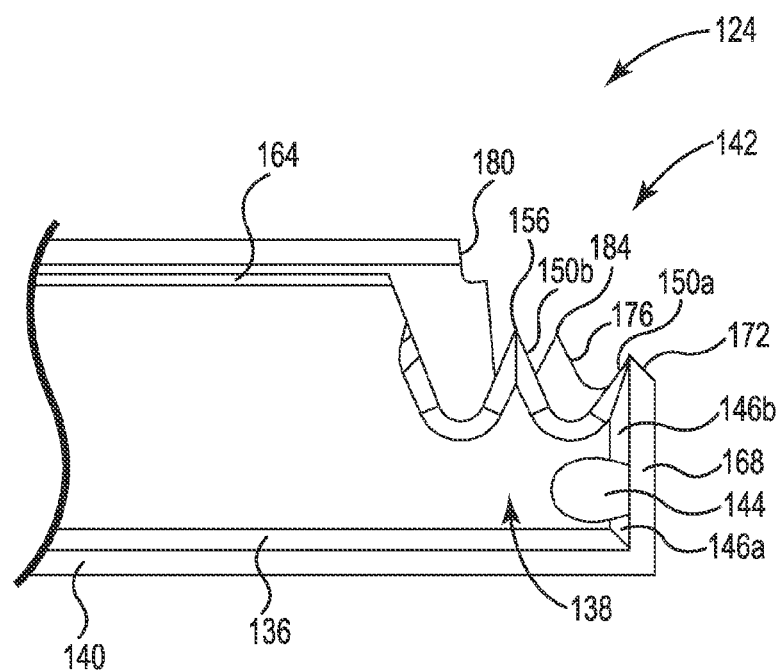
FIGS. 6A and 6B are enlarged cross-sectional and perspective views of an assembled distal end of a cutting implement including the outer blade of FIG. 5A in accordance with principles of the present disclosure.
Figure 6B:
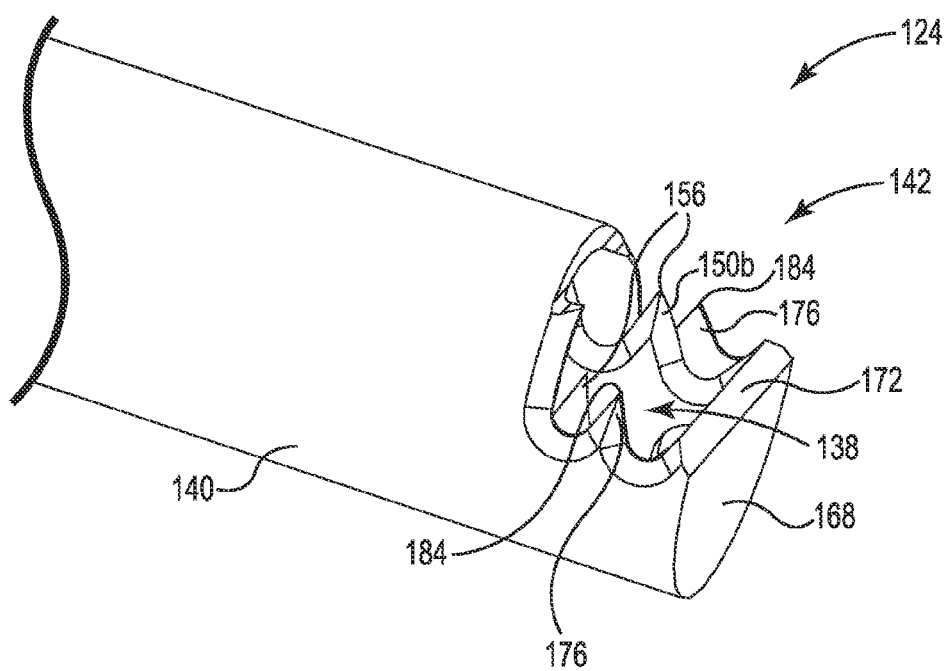
Figure 7A:
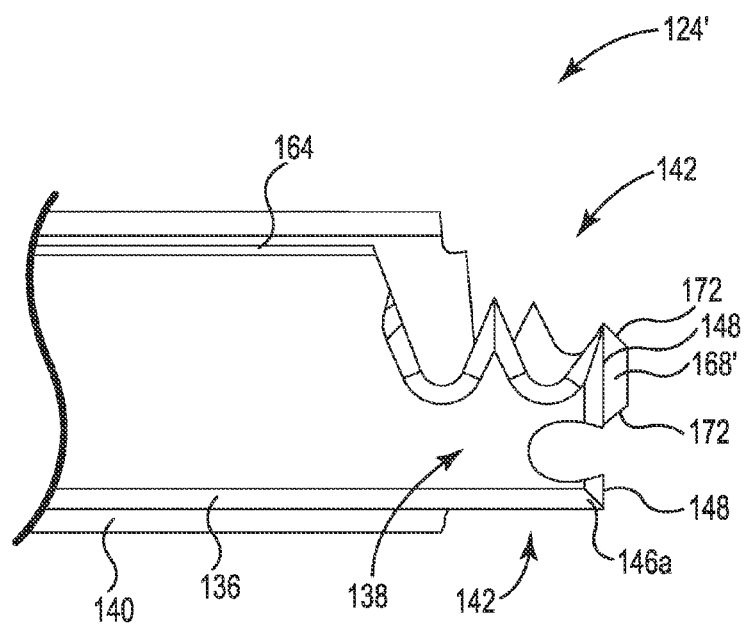
FIGS. 7A and 7B are enlarged cross-sectional and perspective views of an assembled distal end of a cutting implement including the outer blade of FIG. 5B in accordance with principles of the present disclosure.
Figure 7B:
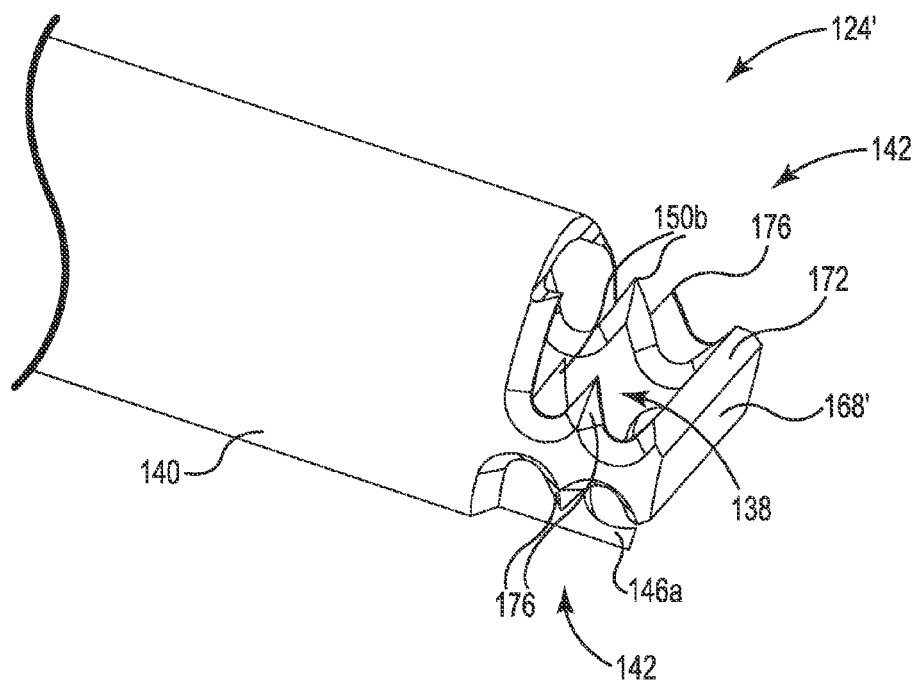

The assembled distal end of a cutting implement 122 including the outer blade 140 of FIG. 5B is illustrated in FIGS. 6A and 6B and the outer blade 140' is included in the assembled distal end illustrated in FIGS. 7A and 7B. In either, as discussed above, the distal portion 160 of the inner blade 136 has a diameter that is larger than the diameter of the main portion 162 of the inner blade 136. The clearance between the outer surface of the distal portion 160 of the inner blade 136 and the inner surface of the outer blade 140 can be 0.0015 inches or less. The outside surface of the inner blade 136 is coated with a biocompatible tungsten-carbide/carbon coating to prevent galling and decrease friction between the inner and outer blades 136, 140. The irrigation channel 164 extends along a length of the inner blade 136 and is fluidly open with the cutting tip 138 in order to maintain irrigation to the cutting tip 138 from between the inner and outer blades 136, 140 and to accommodate the increased diameter of the distal portion 160 of the inner blade 136 within the outer blade 140. With the clearance of 0.0015 inches or less, a shearing of the fibrous tissue between the moving inner blade 136 and the stationary outer blade 140 can occur and tissue is not dragged between the inner and outer blades 136, 140 and eventually torn by multiple rotations of the inner blade 136.

The beveled end edges 148 of the castellations 146a, 146b are configured to directly contact the inner surface the end cap 168 of the outer blade 140 when assembled. The castellated geometry at the distal end of the cutting tip 138 serves to disrupt tissue and drag the tissue toward a low included angle edge on the end cap 168 of the outer blade 140. The end window edge 172 cooperates with the end edges 148 formed on the distal end of the inner blade 136. In use, the distal tips of the castellations 146a, 146b rotationally move against the inside surface of the end cap 168. The castellated geometry provides three hits, or contacts, with the tissue (i.e., one hit per castellation 146a, 146b) during each revolution of the inner blade 136. The spring 44 (see, e.g., FIGS. 3A and 3B) disposed at the proximal end of the inner blade assembly 26 provides a degree of longitudinal movement for the inner blade 136 with respect to the end cap 168. The spring 44 is biased to extend the inner blade 136 distally toward the end cap 168.

The inner and outer blades 136, 140 can be manufactured of a metal, such as stainless steel, or other hard material suitable for use in surgery. The distal portion 160 of the inner blade 136 is fabricated separately from the main portion 162 and then the distal portion 160 and the main portion 162 are coupled together to form the inner blade 136. The main portion 162 is cut to a desired length from tubing. The distal portion 160 is fabricated from a selected non-tubular material member having a mass such as a cube, a bar, or a rod, for example. The mass of the non-tubular material member is selectively removed to form the desired shape of the distal portion 160. The mass of the non-tubular material member can be selectively removed to form the distal portion 160 using micro-machining such as electrical discharge machining (EDM), mechanical machining, chemical machining, micro-electro-mechanical system (MEMS) processing, or other suitable micro-machining method. A bulk, or majority (greater than 50%), of the mass of the non-tubular material member is removed to create a generally tubular shape and the cutting tip 138 of the distal portion 160. Micro-machining, or other suitable method, can be used to create the profile and the sharp angular beveled edges of the castellations 146a, 146b and the teeth 150a, 150b. The distal portion 160 and the main portion 162 are coupled together via welding or other suitable means. As discussed above, the outer diameter $d_2$ of the main portion 162 is smaller than the outer diameter $d_1$ of the distal portion 160. The irrigation channel 164 is machined, or cut, into the distal portion 160 and the main portion 162 of the inner blade 136. A raised fine diamond knurl can be patterned into the proximal end of the inner blade 136.

The outer blade 140 is manufactured from tubing and plate, or sheet, material. The tubing is cut to a desired length to form the tubular side walls of the outer blade 140. In one embodiment, the sheet material is cut to form two thin planar circular discs concentrically attached together, via welding or other means. The two thin planar discs can have different thicknesses. One of the discs has a diameter corresponding to the inside diameter of the outer blade 140 and fits squarely within the outer blade 140 as the inside surface of the end cap 168. The other disc forming the end cap 168, in this embodiment, has a diameter corresponding to, or is otherwise suitable to be mated with, the outside diameter of the outer blade 140 and forms the outside surface of the end cap 168.

The end cap 168 and the tubular side walls of the outer blade 140 are attached together, via welding or other suitable means. The tubular side walls of the tubular member extend along a longitudinal axis and the interior surface of the end cap 168 is perpendicular to the tubular side walls. The interior surface of the tubular side walls intersects squarely with the interior surface of the end cap 168 to form a right angled perimeter. The end cap 168 coupled to the tubular side walls of the outer blade 140 forms squared interior edges at the intersection of the end cap 168 and the tubular sides of the outer blade 140 and avoids the radius that would be created by a boring tool. Alternatively, a single planar disc, or circular plate, can be used to form the end cap 168 having a beveled edge with a smaller and a larger diameter corresponding to the inner and outer diameters of the outer blade 140 to avoid corner radii. Any other method that can create an interior corner without a radius is also acceptable. In one embodiment, the planar disc, or discs, of the end cap 168 are indented in the center to form an inverted conical shape.

The end cap 168 and the tubular walls at the distal end of the outer blade 140 are selectively removed to form the cutting window 142. The outer blade 140 can be micro-machined, or otherwise cut, to form the cutting window 142 with the sharp beveled window edges 172, 174, 178 and window teeth 176. If desired, the markings 170 are etched or otherwise formed into the outer surface of the outer blade 140 at the distal end and a raised fine diamond knurl is patterned into the proximal end of the outer blade 140.

According to aspects of the present disclosure, any burs or weld spatter are removed from the inner and outer blades 136, 140 and the inner and outer blades 136, 140 are flash electro-polished. The inner blade 136 is coupled to the inner hub assembly 42 via welding or other suitable means. The outer blade 140 is coupled to the outer hub assembly 50. The outside surface of the inner blade 136 is coated with a lubricating coating such as a biocompatible tungsten-carbide/carbon coating. The inner blade 136 is inserted into the outer blade 140 such that the cutting tip 138 is positioned to be rotatably exposed at the cutting window 142. The assembled cutting instrument 12 is coupled to the handpiece 20 and the fastener 52 is rotated to removably secure the cutting instrument 12 to the handpiece 20. Tubing 32 can be coupled to the handpiece 20 for the irrigation and aspiration pathways 31a, 31b to fluidly connect the surgical cutting instrument 12 to fluid and suction sources.

Figure 8A:
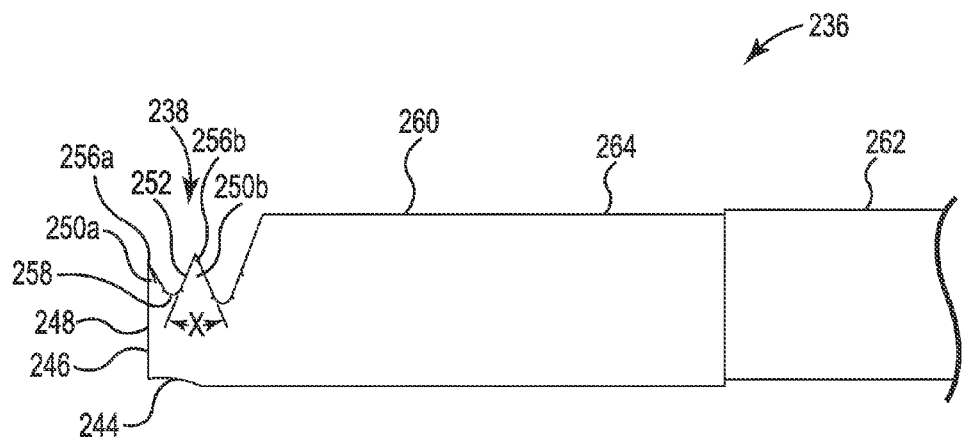
FIGS. 8A through 8C are enlarged side, top, and end views of a distal portion of an inner blade of the cutting implement according to one embodiment of the present disclosure.
Figure 8B:
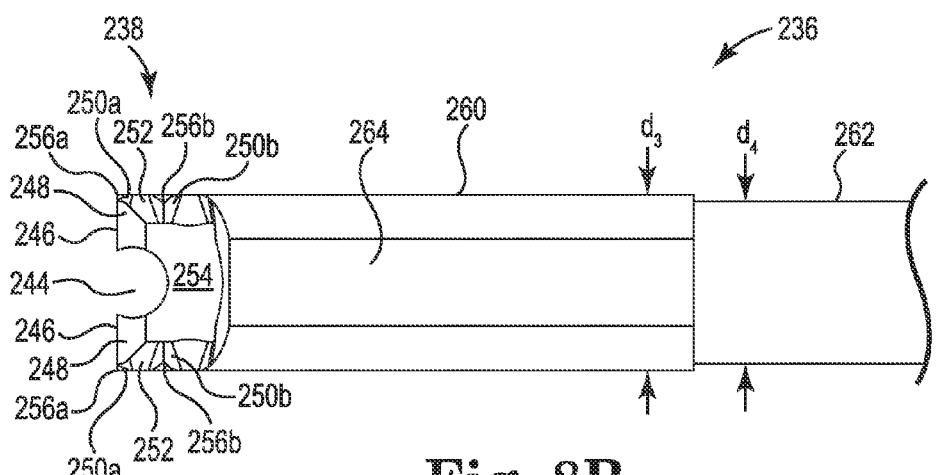
Figure 8C:
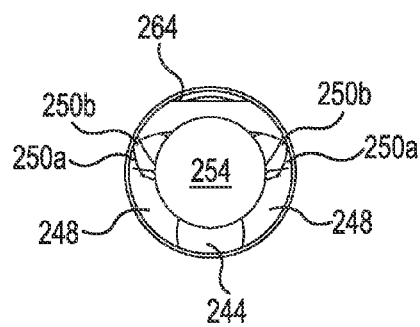
Figure 9A:
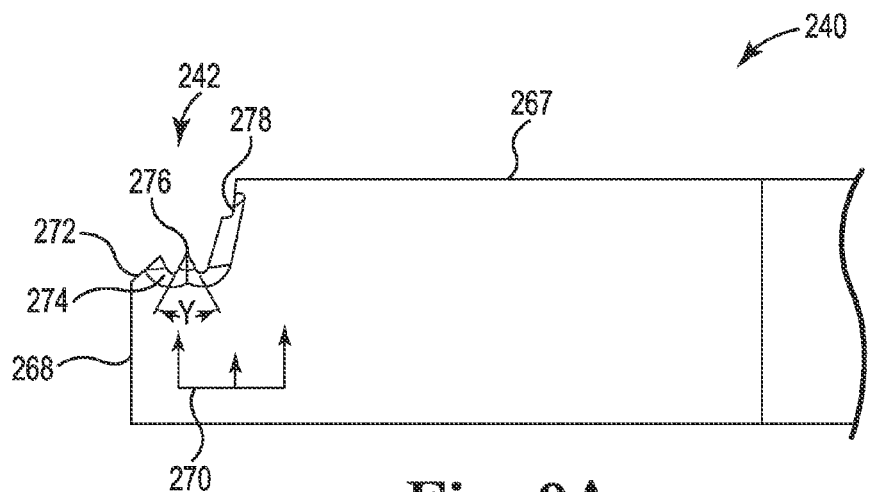
FIGS. 9A through 9C are enlarged side, top, and end views of a distal region of an outer blade of a cutting implement according to one embodiment of the present disclosure.
Figure 9B:
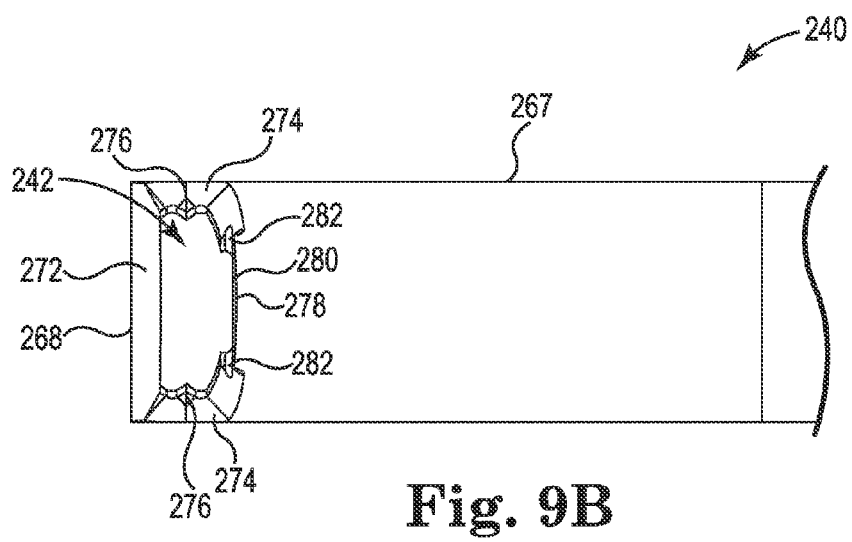
Figure 9C:
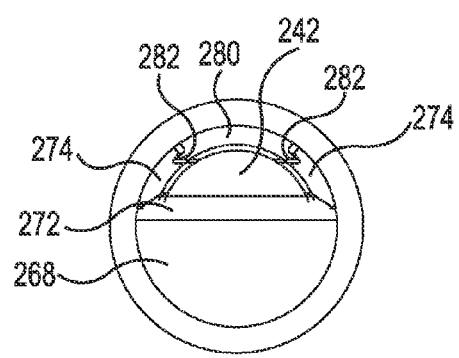
Figure 10A:
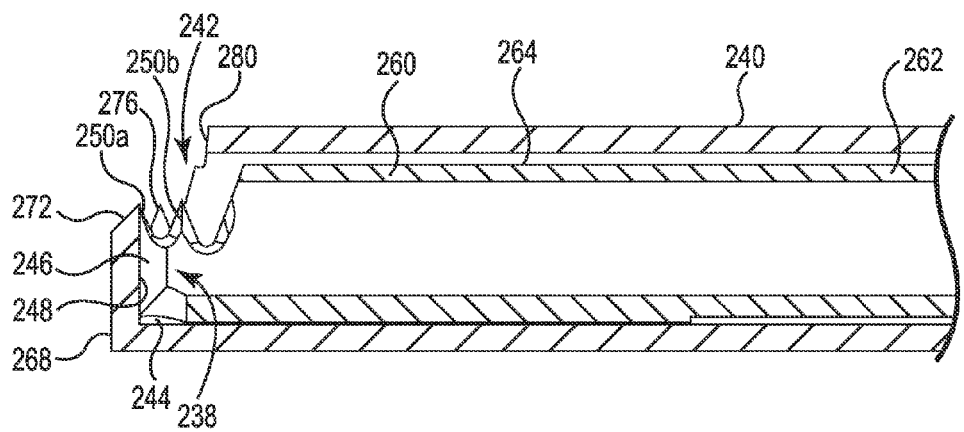
FIGS. 10A and 10B are enlarged cross-sectional and perspective views of an assembled distal portion of the inner blade of FIGS. 8A through 8C and distal region of the outer blade of FIGS. 9A through 9C of a cutting implement in accordance with principles of the present disclosure.
Figure 10B:
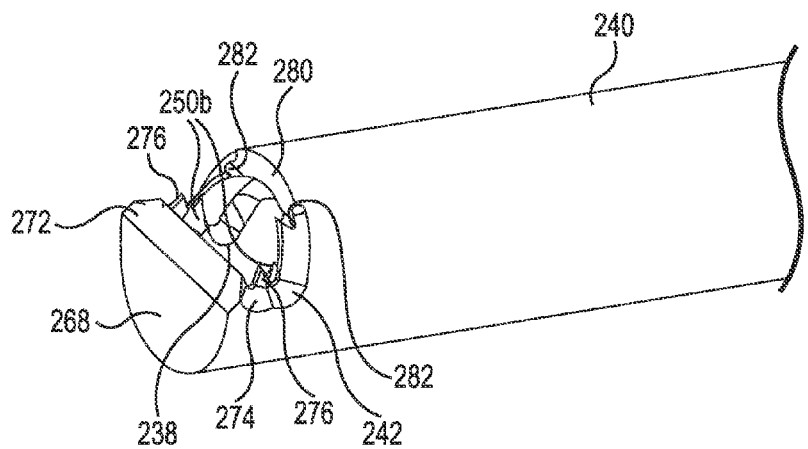

With reference to another embodiment, a cutting implement 222 with a cutter 224 is illustrated in FIGS. 10A and 10B includes a cutting tip 238 of an inner blade 236 illustrated in FIGS. 8A through 8C and the distal region of an outer blade 240 illustrated in FIGS. 9A through 9C according to one embodiment of the present disclosure. As illustrated, upon final assembly, the cutting tip 238 provided on the inner blade 236 is selectively exposed at a cutting window 242 on the distal region of the outer blade 240. Embodiments of the cutting implement 222 and the cutter 224 are particularly suitable for removal of tumors at the interface of the tumor and viable tissue, for example.

With reference to the distal portion of the inner blade 236 illustrated in FIGS. 8A through 8C, the cutting tip 238 includes an open distal end having cutting surfaces formed by radial and longitudinal projections and recesses. An end notch 244 extends between projections 246. In general terms, the projections 246 form the distal end cutting surface of the cutting tip 238. In one embodiment, two opposing side projections 246 at least partially defined by the U-shaped or semi-circular end notch 244 formed between the projections 246. The distal most end of the cutting tip 238 is defined by end edges 248 formed at a distal end of the projections 246. The end edges 248 are radially planar in a plane perpendicular to the longitudinal axis. The end edges 248 are beveled in a longitudinally inward direction to form a sharpened cutting edge. In one embodiment, the end edges 248 are beveled at a 45° angle.

The cutting tip 238 includes teeth 250a, 250b projecting along opposing radial side edges 252 of a central opening 254 of the cutting tip 238. The teeth 250a, 250b are oriented in opposing pairs that are longitudinally aligned to extend toward each other across the central opening 254 of the cutting tip 238 and generally perpendicular to end edges 248 and the projections 246. Edge surfaces of the teeth 250a, 250b are beveled, or angled, towards the interior of the inner blade 236. The teeth 250a are formed on the projections 246 such that tips 256a are aligned with the end edges 248. At least one pair of teeth 250b is included along the radial side edges 252 of the central opening 254. The teeth 250a, 250b can have different heights. Valleys 258 are formed between tips 256a, 256b of teeth 250a, 250b. The teeth 250b are formed to have an angle "$X_1$".

As best illustrated in FIG. 8B, the distal portion 260 has a first outer diameter $d_3$ slightly larger, or greater, than a second outer diameter $d_4$ of an intermediate portion 262. The intermediate portion 262 is similar to intermediate portion 162 described above. In one embodiment, the distal portion 260 is laser welded to the intermediate portion 262. An irrigation channel 264 extends from the central opening 254 of the cutting tip 238 formed on the distal portion 260 to a distal end of the intermediate portion 262. The irrigation pathway extends along the irrigation channel 264 of the cutting tip 238, as described in more detail below.

As discussed above, the first outer diameter $d_3$ of the distal portion 260 is slightly larger, or greater, than the second outer diameter $d_4$ of the intermediate portion 262. For example, in one embodiment, the outer diameter $d_3$ of the distal portion 260 is 0.0615 inches to 0.0620 inches and the outer diameter $d_4$ of the intermediate portion 262 is 0.058+/−0.001 inches. In order maintain irrigation flow between the inner blade 236 and the outer blades 240, the irrigation channel 264 is formed along the distal portion 260 of the inner blade 236. In one embodiment, the irrigation channel 264 is a portion of the outer surface that is planar and is recessed to extend within the thickness of the inner blade 236 between the inside surface and the outside surface. In one embodiment, the irrigation channel 264 is centered between the side edges 252 to be fluidly open at the central opening 254 of the cutting tip 238. The irrigation channel 264 extends from the central opening 254 of the cutting tip 238, along the distal portion 260, to the intermediate portion 262 of the inner blade 236. In one embodiment, the distal portion 260 has a length of 0.200 inches and the opening 254 extends approximately 0.040 inches along the longitudinal axis and the distal portion 260.

With reference to FIGS. 9A through 9C, the cutting window 242 is formed at the distal region 267 of the outer blade 240 is defined by shearing edges on the tubular sides and an end cap 268 of the outer blade 240. The outer blade 240 is similar to outer blade 140 described above. The end cap 268 can be shaped as a segment or a circular zone, for example, at the distal end of the tubular body of the outer blade 240. In this manner, both end cutting and side cutting, or shearing, surfaces are provided. The geometry of the cutting window 242 is configured to avoid clogging. For example, the cutting window 242 can have a length equivalent to the inner diameter of the inner blade 236 in order to avoid cutting off pieces of tissue large enough to clog the inner blade 236 and disrupt cutting. The outer surface of the distal region 267 can include markings 270 to visually indicate a depth of the cutting tip 238, and thus the cut, with respect to the tissue. For example, the markings 270 could be placed to indicate a cutting depth of 0.5 millimeter, 1.0 millimeter, 1.5 millimeters, etc. with lines and/or numbers.

In one embodiment, the end cap 268 is planar and the outer blade 240 is cylindrical rather than hemispherical at the distal region 267. The planar end cap 268 is perpendicular to cylindrical side walls of the distal region 267. The end cap 268 is joined to the tubular side walls of the distal region 267 of the outer blade 240 to squared off interior surfaces along the perimeter intersection of the end cap 268 and the side walls of outer blade 240. In other words, the interior of the distal region 267 of the outer blade 240 at the intersection of the end cap 268 and the tubular side walls of the outer blade 240 forms a right angle (i.e., 90°), without a radius. The squared off surfaces of the end cap 268 and side walls expose a maximum surface area to the cutting end edges 248 of the projections 246 of the cutting tip 238 (see, e.g., FIG. 10A). Due to the increased cutting surface area, cutting of the tissue occurs more quickly as compared to that of a hemispherical end cutter or a cavitational ultrasonic surgical aspirator (CUSA).

With continued reference to FIGS. 9A through 9C, an end window edge 272 is formed on the end cap 268. In one embodiment, the end window edge 272 is positioned such that the resulting opening is less than half of the end cap 268. In one embodiment, the end window edge 272 is linear, extending across a width of the outer blade 240 to define an open semi-circular shape on the end cap 268. The end window edge 272 is beveled, or angled, towards an exterior of the outer blade 240.

Side window edges 274 extend from the end window edge 272 along the tubular sides of the distal region 267. The side window edges 274 are serrated to include window teeth 276. The window teeth 276 are disposed on opposing radial sides of the cutting window 242. Similar to the teeth 250a, 250b on the inner blade 236, the window teeth 276 are oriented in opposing pairs that are longitudinally aligned to extend toward each other across the cutting window 242 and extend generally perpendicular to the end cap 268. The cutting window 268 includes outwardly beveled edges. For example, the side window edges 274, including edge surfaces of the window teeth 276 are beveled, or angled, towards the exterior of the outer blade 240. In one embodiment, an inner portion of the side window edges 274 is sharpened at an angle different from the outer portion of the side window edges 274. A suitable quantity of window teeth 276 are included on the cutting window 242 to correspond with, and interact with, the quantity of teeth 250 on the cutting tip 238. In one embodiment, a single pair of window teeth 276 and a single pair of teeth 250b are provided. An angle "$Y_1$" formed by the sides of the window teeth 276 complements the angle "$X_1$" of the teeth 250b of the cutting tip 238. For example, when the angle "$Y_1$" of the window teeth 276 is 57° and the angle "$X_1$" of the teeth 250b is 46°. Regardless, the tips of the window teeth 276 are longitudinally offset from the tips 256a, 256b.

The cutting window 242 includes a top window edge 278 extending between the side window edges 274, opposite the end window edge 272, to form the cutting window 242. The top window edge 278 includes a center section 280 and opposing recesses 282 to form additional shearing surfaces. As best illustrated by FIGS. 9A and 9B, the center section 280 can be slightly angled and the recesses 282 are angled distinctly from both the adjacent side window edges 274 and the center section 280 to create additional shearing, or cutting, surface.

Upon final assembly, as best shown in FIGS. 10A and 10B, the cutting tip 238 is positioned at the cutting window 242 with the two components being rotatable relative to one another as discussed above. The cutting tip 238 includes surfaces or edges, including those formed by projections 246 and teeth 250a, 250b, for engaging tissue via the cutting window 242 in the distal end of the outer blade 240. The edges forming the cutting tip 238 are beveled inwardly and the edges defining the cutting window 242 are generally beveled outwardly to form cooperating shearing surfaces. As the inner blade 236 is rotatably driven at its proximal end, for example by the motorized handpiece 20, the surface or edge of the cutting tip 238 will cooperate with the cutting window 242 in the outer blade 240 to shear, cut, or shave the tissue. The end edges 248 of the cutting tip 238 directly contact the end cap 268 of the outer blade 240 to provide end cutting. The spring 44 of the inner hub assembly 42 biases the end edges 248 toward the end cap 268. In general terms, the inner geometry of the cutting tip 238 is designed to impale the tissue as the cutting tip 238 is rotated and provides both end cutting and side cutting via cylindrical geometry. As discussed further below, peripheral edges of the cutting tip 238 opening formed are positioned adjacent cutting window 242 such that the cutting edges of the cutting tip 238 can engage bodily tissue through the cutting window 242 and pull the tissue against the edges defining the cutting window 242 to shear the tissue. Micro-machining, or other suitable method, can be used to create the profile and the sharp angular and edges of the cutting tip 238 and cutting window 242.

As discussed above, the distal portion 260 of the inner blade 236 has a diameter $d_3$ that is larger than the diameter $d_4$ of the intermediate portion 262 of the inner blade 236. For example, the outer diameter $d_3$ of the distal portion 260 can be 0.0620 inches and the outer diameter $d_4$ of the intermediate portion 262 can be 0.058+/−0.001 inches. The clearance between the outer surface of the distal portion 260 of the inner blade 236 and the inner surface of the outer blade 240, particularly the distal region 267, can be 0.002 inches or less and, in particular, at the cutting window 242 can be 0.000093 inches to 0.00109 inches. As assembled, the outside surface of the inner blade 236 is coated with a biocompatible tungsten-carbide/carbon coating to prevent galling and decrease friction between the inner and outer blades 236, 240. The irrigation channel 264 extending along the distal portion 260 of the inner blade 236 and is fluidly open with the cutting tip 238 in order to maintain irrigation to the cutting tip 238 from between the inner and outer blades 236, 240 and to accommodate the increased diameter of the distal portion 260 of the inner blade 236 within the outer blade 240. With the clearance of 0.000093 inches to 0.00109 inches at the cutting window 242, a shearing of the fibrous tissue between the moving inner blade 236 and the stationary outer blade 240 can occur and tissue is not dragged between the inner and outer blades 236, 240 and to be eventually torn by multiple rotations of the inner blade 236.

The inner and outer blades 236, 240 can be manufactured of a metal, such as stainless steel, or other hard material suitable for use in surgery. The distal portion 260 of the inner blade 236 is fabricated separately from the intermediate portion 262 and the distal region 260 is fabricated separately from the remainder of the outer blade 240. The distal region 267 having the cutting window 242 can be formed of a material different from, and having a Rockwell hardness greater than, the remainder of the outer blade 240. For example, the distal region 267, including the end cap 268, can be formed of 440C stainless steel (s.s.) with a hardness above 50 HRC and the remainder of the outer blade 240 can be formed of 304L s.s. tubing. Similarly, the distal portion 260 having the cutting tip 238 can be formed of a material different from, and having a Rockwell hardness greater than, the remainder of the inner blade 236. For example, the distal portion 260 can be formed of 440C s.s. with a hardness above 50 HRC and the remainder of the inner blade 236 can be formed of 304L s.s. tubing. Micro-machining such as electrical discharge machining (EDM), electrochemical machining (ECM), mechanical machining, chemical machining, or other suitable micro-machining method can be used to form the cutting inner and outer blades, in particular, the cutting tip 238 and cutting window 242. In one embodiment, the distal region 267 is laser beam welded to the remainder of the outer blade 240 and the distal portion 260 is laser beam welded to the intermediate portion 262 of the inner blade 236.

Figure 11A:
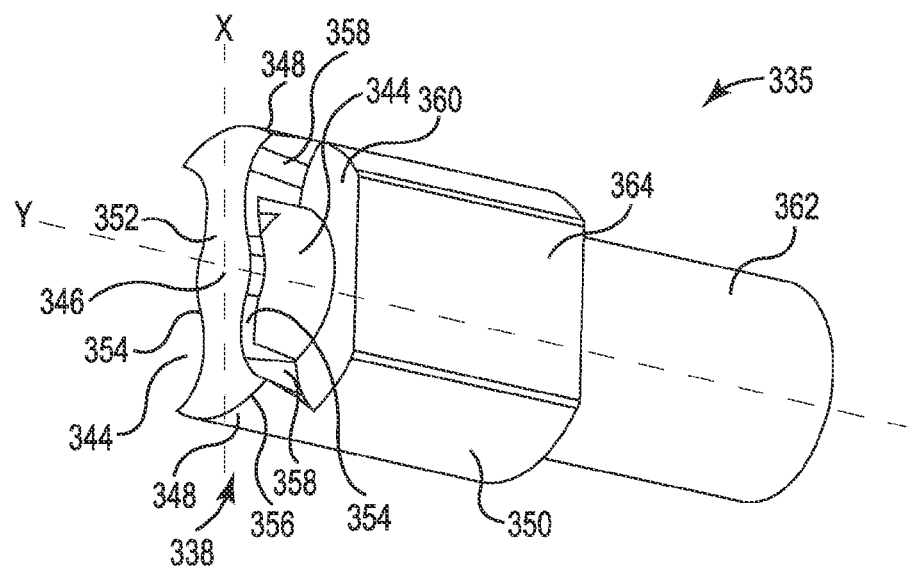
FIGS. 11A and 11B are enlarged perspective and top views of a distal portion of an inner blade of the cutting implement according to another embodiment of the present disclosure.
Figure 11B:
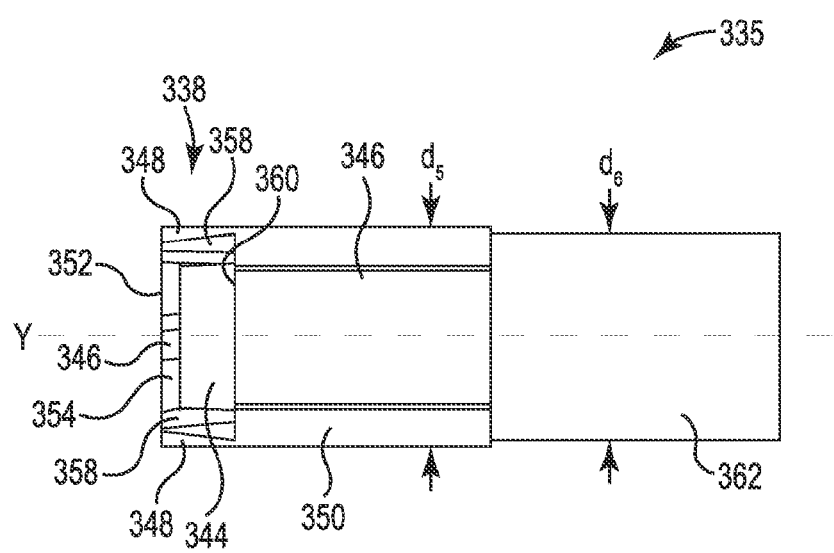
Figure 12A:
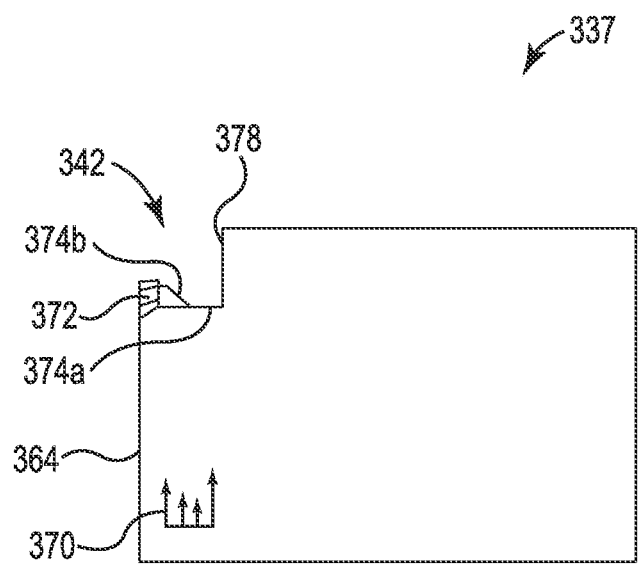
FIGS. 12A and 12B are enlarged side and cross-sectional views of a distal region of an outer blade of a cutting implement according to another embodiment of the present disclosure.
Figure 12B:
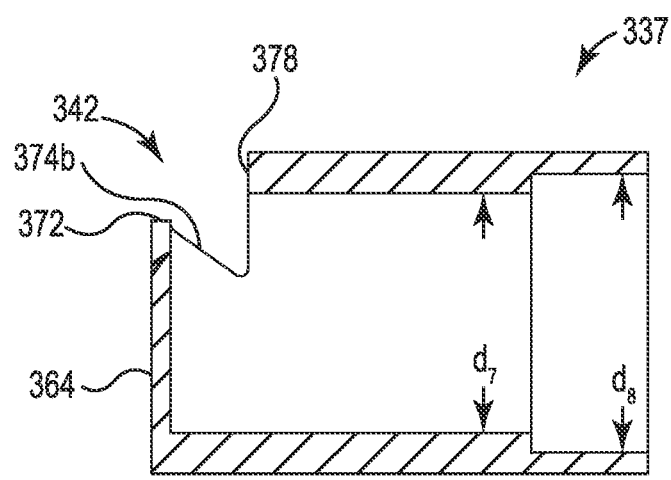
Figure 13A:
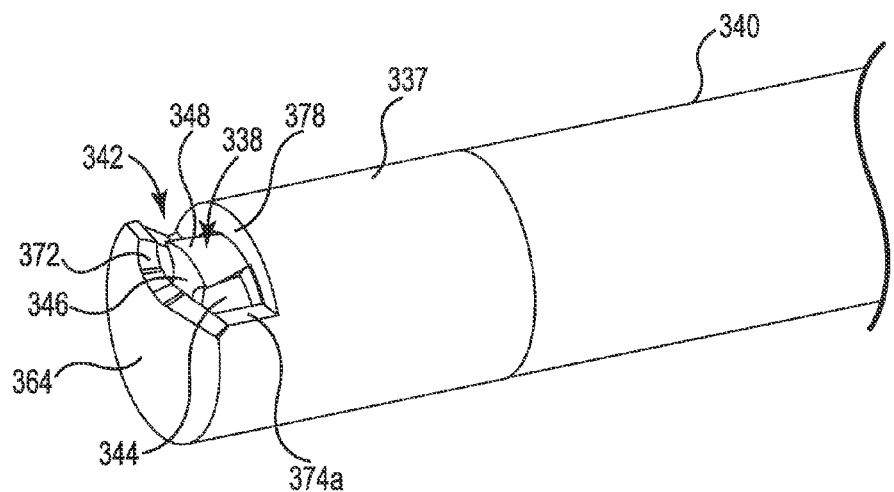
FIGS. 13A and 13B are enlarged perspective and cross-sectional views of an assembled distal portion of the inner blade of FIGS. 11A and 11B and the distal region of the outer blade of FIGS. 12A and 12B of a cutting implement in accordance with principles of the present disclosure
Figure 13B:
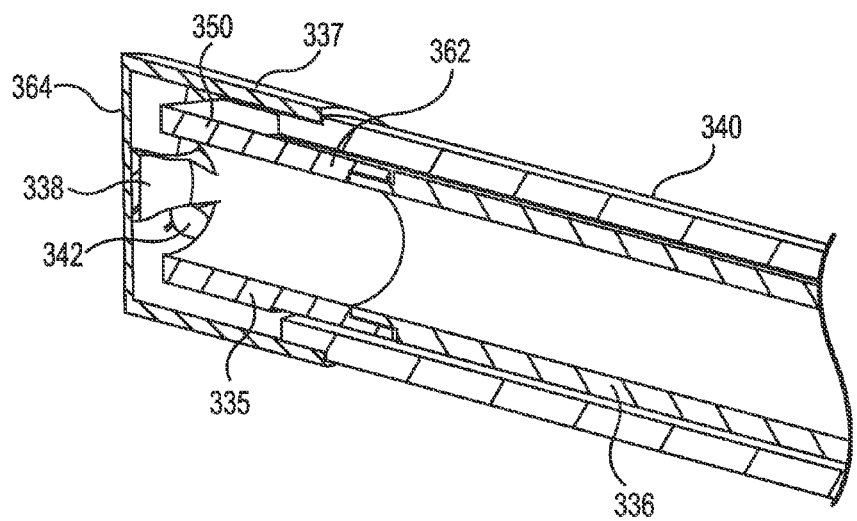

Another embodiment of an assembled distal end of a cutting implement 322, in accordance with principles of the present disclosure, is illustrated in FIGS. 13A and 13B. FIGS. 11A and 11B are enlarged cross-sectional and perspective views of a distal portion 335 of an inner blade 336 of FIGS. 13A and 13B and a distal region 337 of an outer blade 340 is illustrated in FIGS. 12A and 12B. As illustrated, upon final assembly, a cutting tip 338 of the inner blade 336 is selectively exposed at a cutting window 342 of the outer blade 340. Aspects of the inner blade 336 and outer blade 340 are similar to the inner blade 136, 236 and outer blade 140, 240, respectively.

With reference to FIGS. 11A and 11B, the cutting tip 338 includes openings 344 defined by cutting surfaces of the cutting tip 338. The cutting tip 338 includes a terminal end portion 346 and opposing side portions 348. The side portions 348 extend distally, or along a longitudinal axis of the inner blade 336, to connect the terminal end portion 346 with the body of the distal portion 335. Openings 344 are defined by the cutting surfaces of the terminal end portion 346 and side portions 348 and provide side and end cutting and fluid pathways. As illustrated in FIG. 11A, a double-edged cutting surface of the cutting tip 338 is formed.

An outer surface of the side portions 348 is arcuate and maintains an outer circumference of the first section 350 of the distal portion 335. The terminal end portion 346 has a top surface 352 defined by curvilinear side edges 354 extending between opposing end portions 348. In one embodiment, an interior surface opposite the top surface 352 of the terminal end portion 346 is also planar. The top surface 352 intersects with the side portions 348 to form the arcuately shaped end edges 356. In one embodiment, the curvilinear side edges 354 of the top surface 352 are symmetrical about a "y" axis formed along the planar top surface 352, and perpendicular to the longitudinal axis, or "x" axis, of the inner blade 336. In one embodiment, each of the side edges 354 includes a semicircular center portion and opposing concave portions. In other words, the concave portions of the side edges 354 extend between the center portions and the end edges 356. In one embodiment, the concave portions joined on opposing ends of the center portion of one side edge 354 have the same radii, although differing radii can also be acceptable.

Sides 358 of the side portions 348 are tapered, or angled, curvilinearly inward from the intersecting planar top surface 352 to an opening surface 360 to form sharpened cutting edges. In one embodiment, the opening surface 360 is planar and parallel to the top surface 352. As illustrated best in FIG. 11A, the tapered sides 358 of the side portions 348 are smooth and without intermediate projections or teeth. In one embodiment, the terminal end portion 346 has a thickness of 0.0050+/−0.0005 inches between the top surface and the opposing surface and the top surface 352 of the cutting tip 338 is positioned 0.020+/−0.001 inches from the opening surface 360 to form a longitudinal length of the openings 344. Openings 344 are fluidly open to the central lumen of the inner blade 336 as described further below.

As best illustrated in FIG. 11B, the distal portion 335 includes the first section 350 having a first outer diameter $d_5$ slightly larger, or greater, than a second outer diameter $d_6$ of a second section 362. For example, in one embodiment, the outer diameter $d_5$ of the first section 350 is 0.0620 inches and the outer diameter $d_6$ of the second section 362 is 0.058+/−0.001 inches.

In order maintain irrigation flow between the inner blade 336 and the outer blade 340, the irrigation channel 364 is formed along the first section 350 of the distal portion 335 of the inner blade 336. The irrigation pathway extends along the irrigation channel 364 to the cutting tip 338, as described in more detail below. In one embodiment, the irrigation channel 364 is a portion of the outer surface that is planar and is recessed to extend within the thickness of the inner blade 336 (i.e., between the inside surface and the outside surface). In one embodiment, the irrigation channel 364 has slightly chamfered longitudinal edges. In one embodiment, there are two opposing irrigation channels 364, one each centered between the side portions 348 of the cutting tip 338 and each fluidly open at the openings 344 of the cutting tip 338. The irrigation channels 364 extend from the openings 344 of the cutting tip 338, along the first section 350, to the second section 362 of the inner blade 336. In one embodiment, the first section 350 has a length of 0.060 inches along the "y", or longitudinal, axis.

With additional reference to FIG. 13B and similar to the previous embodiments, the distal portion 335 can be formed separately from, and joined together with, an intermediate portion 365. In one embodiment, the second section 362 has an increased proximal inner diameter suitable to accommodate an outer diameter of the intermediate portion 365 extendable within the distal portion to a predetermined distance. In one embodiment, a lip of the intermediate portion 365 extends within the second section 362 and distal portion 335 is laser welded to the intermediate portion 365. In one embodiment, the proximal inner diameter of the second section 362 is 0.500+/−0.0005 inches while the remainder of the distal portion 335 has an inner diameter of 0.042+/−0.001 inches.

With reference to FIGS. 12A and 12B, the cutting window 342 formed at the distal region 337 of the outer blade 340 is defined by shearing edges on the tubular sides and an end cap 368 of the outer blade 340. In this manner, both end cutting and side cutting, or shearing, surfaces are provided. The geometry of the cutting window 342 is sized and shaped to avoid clogging and maintain a continuously open fluid pathway between the exterior and the interior central lumen of the inner blade 336. For example, the cutting window 342 can have a length along the longitudinal axis approximately equivalent, or slightly larger than, the distance between the top surface 352 and the opening surface 360 of the cutting tip 338 in order to avoid cutting off pieces of tissue large enough to clog the inner blade 336 and disrupt cutting. The outer surface of the distal region 337 can include markings 370 to visually indicate a depth of the cutting tip 338, and thus the cut, with respect to the tissue. For example, the markings 370 could be placed to indicate a cutting depth of 0.5 millimeter, 1.0 millimeter, 1.5 millimeters, etc. with lines and/or numbers.

The end cap 368 is planar and the outer blade 340 is cylindrical rather than hemispherical at the distal region 337. An interior surface of the tubular side wall and the end cap 368 of the distal region 337 are smooth. The planar end cap 368 is perpendicular to cylindrical side walls of the distal region 337. The end cap 368 is joined to the tubular side walls of the distal region 337 of the outer blade 340 with squared off interior surfaces along the perimeter intersection of the end cap 368 and the side walls of outer blade 340. In other words, the interior of the distal region 337 of the outer blade 340 at the intersection of the end cap 368 and the tubular side walls of the outer blade 340 forms a right angle (i.e., 90°), without a radius. The squared off surfaces expose a maximum surface area to the cutting end edges 356 of the cutting tip 338. Cutting of the tissue occurs more quickly in the present embodiments as compared to that of a hemispherical end cutter or a CUSA due to the increased cutting surface area.

With continued reference to FIGS. 12A and 12B, an end window edge 372 is formed on the end cap 368 to partially define the open shape of the cutting window 342 on the end cap 368. In one embodiment, the end window edge 372 is positioned such that the resulting opening is less than half of the end cap 368. In one embodiment, the end window edge 372 is generally non-linear, extending across a width of the outer blade 340. The end window edge 372 is curved and a varying surface area of the cutting tip 338 is exposed at the cutting window 342 as the cutting tip 338 rotatably passes through the cutting window 342. In one embodiment, two cutting windows 342 are included (not shown). As best illustrated in FIG. 13A, the end window edge 372 is beveled, or angled, towards an exterior of the outer blade 340.

Side window edges 374a, 374b extend from the end window edge 372 along the tubular sides of the distal region 337 of the outer blade 340. The side window edges 374a, 374b can extend from the interior surface to an exterior surface of the tubular side walls flatly, or squarely (i.e., without beveled edges) or can be beveled outwardly. In one embodiment, as illustrated in FIG. 12A, the side window edge 374a extends parallel to the longitudinal axis of the outer blade 340. In one embodiment, the side window edge 374b extends from the end cap 368 at an acute angle that decreases the surface area of the tubular side walls as the side window edge 374b extends away from the end cap 368. In another embodiment, the side window edge 374b extends from the end cap 368 parallel to the longitudinal axis for a predetermined distance and then extends at an acute angle that decreases the surface area of the tubular side walls as the side window edge 374b extends away from the end cap 368.

The cutting window 342 includes a top window edge 378 extending between the side window edges 374, opposite the end window edge 372, to form the cutting window 342. In one embodiment, the top window edge 378 extends along a partial circumference of the tubular body in a plane parallel to the end cap 368. The end window edge 372, the side window edges 374a, 374b, and the top window edge 378 all form shearing surfaces defining the cutting window 342.

The distal region 337 has an outer diameter that is constant, or same. The interior of the distal region 337 has a first inner diameter $d_7$ and a second inner diameter $d_8$. The second inner diameter $d_8$ is greater than the first inner diameter $d_7$. The second inner diameter $d_8$ of the distal region 337 is sized and shaped to accommodate a lip of the outer blade 340.

Upon final assembly, as best shown in FIGS. 13A and 13B, the cutting tip 338 is positioned at the cutting window 342 with the two components being rotatable relative to one another as discussed above. As the inner blade 336 is rotatably driven at its proximal end, for example by the motorized handpiece 20, the surfaces or edges of the cutting tip 338 of the inner blade 336 will cooperate with the cutting window 342 in the outer blade 340 to shear, cut, or shave the tissue. In general terms, the inner geometry of the cutting tip 338 is designed to impale the tissue as the cutting tip 338 is rotated and provides both end cutting and side cutting via cylindrical geometry and end and side openings of the cutting window 342 and cutting tip 338. The end edges 356 of the cutting tip 338 directly contact the end cap 368 of the outer blade 340 to provide end cutting. The spring 44 of the inner hub assembly 42 biases the end edges 356 toward the end cap 368. The direction of the cutting tip 338 rotation is toward the side window edge 374b, and thus, away from side window edge 374a. In this manner, the tissue impaled by the cutting tip 338 is rotated toward side window edge 374b where it is sheared off. As discussed further below, peripheral edges of the cutting tip 338 are positioned adjacent cutting window 342 such that the cutting edges of the cutting tip 338 can engage bodily tissue through the cutting window 342 and pull the tissue against the edges defining the cutting window 342 to shear the tissue. Micro-machining, such as ECM or EDM, for example, can be used to create the profile and the sharp angular and beveled edges of the cutting tip 338 and the cutting window 342.

The outside surface of the inner blade 336, or the inside surface of the outer blade 340, is coated with a biocompatible tungsten-carbide/carbon coating to prevent galling and decrease friction between the inner and outer blades 336, 340. The irrigation channel 364 extends along the first section 350 of the inner blade 336 and is fluidly open with the cutting tip 338 in order to maintain irrigation to the cutting tip 338 from between the inner and outer blades 336, 340 and to accommodate the increased diameter of the first section 350 of the inner blade 336 within the outer blade 340. With the clearance of 0.000093 inches to 0.00109 inches at the cutting window 342, a shearing of the fibrous tissue between the moving inner blade 336 and the stationary outer blade 340 can occur and tissue is not dragged between the inner and outer blades 336, 340. Embodiments of the cutting device, in accordance with aspects of the present disclosure, are suitable for cutting tumors ranging from the very soft to the very fibrous. The flat, or planar, shaped distal cutting ends of the inner and outer blades are suitable for digging into and impaling tissue that is not likely to deflect under vacuum pressure.

As with the previous embodiments, the inner and outer blades 336, 340 can be manufactured of a metal, such as stainless steel, or other hard material suitable for use in surgery. The distal portion 335 of the inner blade 336 is monolithically fabricated of a single piece of material and subsequently coupled to the intermediate portion 365. Similarly, the distal region 337 is monolithically fabricated of a single piece of material and subsequently coupled to the outer blade 340. The distal region 337 having the cutting window 342 can be formed of a material different from, and having a Rockwell hardness greater than, the remainder of the outer blade 340. For example, the distal region 337, including the end cap 368, can be formed of 440C stainless steel (s.s.) with a hardness above 50 HRC and the remainder of the outer blade 340 can be formed of 304L s.s. tubing. Similarly, the distal portion 335 having the cutting tip 338 can be formed of a material different from, and having a Rockwell hardness greater than, the remainder of the inner blade 336. For example, the distal portion 335 can be formed of 440C s.s. with a hardness above 50 HRC and the remainder of the inner blade 336 can be formed of 304L s.s. tubing. In one embodiment, the distal region 337 is laser beam welded to the remainder of the outer blade 340 and the distal portion 335 is laser beam welded to the intermediate portion 365 of the inner blade 336.

Figure 14A:
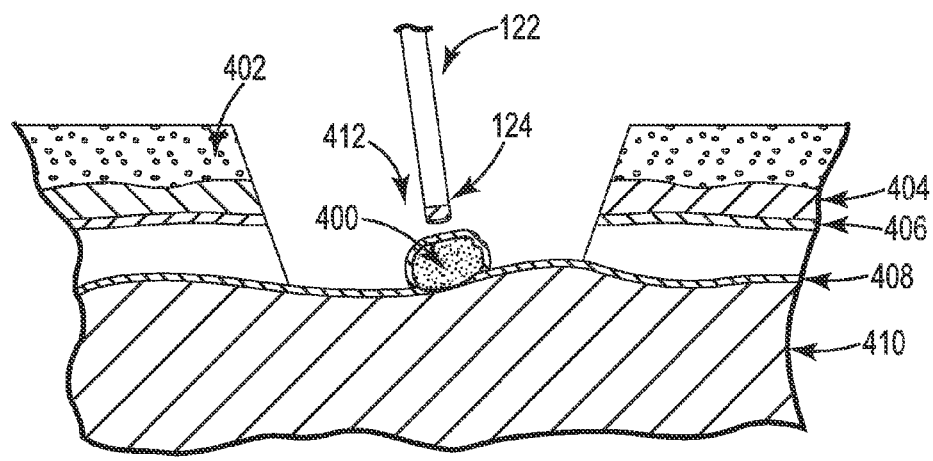
FIGS. 14A and 14B illustrate use of the system of FIG. 1 in surgically removing a brain tumor.
Figure 14B:
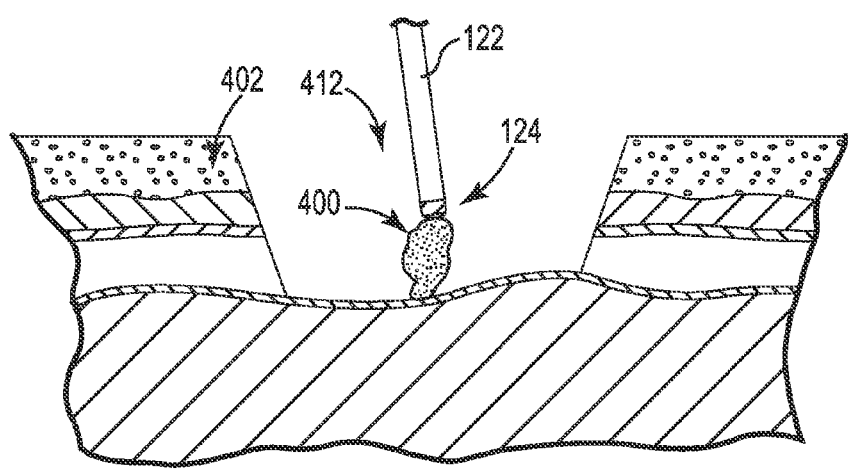

In accordance with the above disclosure, and with further reference to FIGS. 14A and 14B, the system 10 is highly useful in the surgical treatment (i.e., removal) of intracranial and spinal tumors (as well as possibly other surgical procedures). In this regard and by way of example, treatment of a tumor 400 in a cranial procedure in accordance with aspects of the present disclosure includes forming an access opening in the patient's skull 402 (e.g., a conventional craniotomy). As a point of reference, FIG. 14A schematically illustrates other anatomy, including the dura 404, the arachnoid 406, the pia 408, and the cortex 410. The brain tumor 400 is shown as projecting from a natural anatomy of the cortex 410. With other procedures, the brain tumor 400 may be internal or embedded within the cortex 410 (or other brain tissue). Regardless, once a target site 412 at which the brain tumor 400 is located has been exposed, the system 10 is operated to remove at least some, preferably all, of the brain tumor 400.

Once a target site 412 at which the brain tumor 400 has been exposed, the system 10 is operated to remove at least some, preferably all, of the brain tumor 400, regardless of whether it is a soft or a fibrous tumor. In accordance with aspects of the present disclosure, embodiments of the cutting implement 122 are particularly suitable for removal of the bulk of a tumor 400 and embodiments of the cutting implement 222, 322 are particularly suitable for removal of tumors at the interface of the tumor and viable tissue, although the embodiments are suitable for use elsewhere as well.

Operation of the cutting system 10 can be explained with additional general reference to FIG. 1. The user selects the desired size and cutting configuration of the cutting implement 22 (e.g., cutting implement 122) as appropriate for the target area to be removed and assembles it with the handpiece 20. The blade assemblies 26, 28 are inserted into the handpiece 20 and rotated to engage the fastener 52 with the handpiece 20. The fluid pathways 31a, 31b from the cutting instrument 12 are fluidly connected to the IPC 14, fluid source 16, and negative pressure source 18. Electrical connection of the surgical instrument 12 to the IPC 14 is also made. The IPC 14 electronically recognizes the cutting implement 22 and sets the rotational speed and irrigation flow to correspond to the specific cutting implement 14 requirements. For example, cutting tip 138 may operate optimally at a greater or lesser rotational speed than cutting tip 238.

By way of example, and with reference to the embodiment of FIGS. 14A-14B, the assembled surgical cutting instrument 12 is deployed to the target site 412. For example, the instrument 12 with the cutting implement 122 is deployed to a target site 412, with the user manipulating the handpiece 20 to achieve a desired position of the cutting implement 122 relative to the tumor or fibrous tissue. Once the surgeon positions the cutter 24 of the cutting implement 22 adjacent the tumor 400, the surgeon manipulates the handpiece 20 so as to position the cutting window 142 adjacent and/or into the brain tumor 400. Depending upon the particular location of the tumor 400, the cutting implement 122 can be manipulated sideways across the tumor 400 or downward without overtly twisting/contortion of the surgeon's hand(s). Additionally, the window orientation assembly 30 can be manipulated to rotate the cutting window 142 around the longitudinal axis.

Rotation of the inner blade 136 of the cutting implement 122 is effectuated by activation through the IPC 14. The controller/IPC 14 enables selective rotational control over the inner blade 136 to cause high-speed rotation of the cutting implement 122 for debriding or otherwise cutting the target tissue. The location of the cutting window 142 at the distal end, for example with openings in both the terminal end cap 168 and side walls of the distal region 167 provides the ability to resect fibrous tissue in lateral planes as well as end planes. In one embodiment, the cutting window 142 is open only at the end cap 168 for cutting on an end plane. The motor housed within the handpiece 20 effectuates a non-oscillating tumor cutting operation of the inner blade 136.

Fluid is continuously supplied to the cutting tip 138 and cutting window 142 by the fluid source 16 via the fluid pathway between the inner and outer blades 136, 140 including along the irrigation channel 164. In this manner irrigation fluid is introduced to the cutting site 412. The aspiration control hole 34 is manually operated by the user to selectively effectuate aspiration at the cutting window 142 generated by the negative pressure source 18. The aspiration control hole 34 provides the user the ability to vary the rate or level of aspiration at the cutting tip 138 by slidably positioning the user's thumb or finger over the opening of the aspiration control hole 34. Accordingly, when the hole 34 is fully covered, maximum aspiration occurs at the cutting window 142 and when the opening is fully exposed, little or no aspiration occurs. In accordance with aspects of features of this disclosure, degrees of intermediate aspiration at the cutting window 142 can also be achieved.

The aggressiveness of the tissue removal can be controlled by the size and blade configuration as well as the controlled amount of aspiration. For example, embodiments of the cutting implement 122 are particularly suitable for rapid removal of the bulk of the tumor 400 and embodiments of the cutting implement 222, 322 are particularly suitable for removal of tumors at the interface of the tumor 400 and viable tissue. With continued reference to the example of cutting implement 122, the cutting window 142 is open to the aspiration pathway at all times. As the surgeon approaches an area of the patient's brain that the tumor 400 is to be removed, the surgical cutting instrument 12 is moved generally toward the target site 412 with the surgeon's finger removed from the aspiration control hole 34. In this manner, there is no negative pressure, or aspiration at the target site 412. As the cutting implement 122 nears the target site 412 and the surgeon desires to approximate the location of the cutter 124 to the target site 412, the surgeon can gradually or fully close down by partially or fully covering the aspiration control hole 34 with their finger, in this manner, the negative pressure, or suction, provides intimate contact of the tissue with the cutter 124. This allows for neurosurgery or spine surgery on the dura 404 without damage to the dura 404, for example.

The sweep of the cutting tip 138 travels through empty space created by the geometry of the cutting window 142. The sweep of the cutting tip 138 within the cutting window 142 permits cutting when suction is not effective at pulling tissue into the cutting window 142 as can occur with fibrous tissues. The cutting window(s) 142 are open to the aspiration pathway at all times. Suction is used to draw the cut tissue and irrigant from within the cutting window 142 for removal. Suction of the tissue into the cutting window 142 is not required in order to cut the tissue. Fibrous tissue will often not deflect sufficiently under ordinary hospital suction (approximately 300 mm Hg or less). A mixture to irrigant and resected tissue is drawn down the lumen of the inner blade 136 via suction and travels from distal to proximal end and exits out through the handpiece 20.

With additional reference to the assembled cutter 124 in FIGS. 6A-6B, the teeth 150a, 150b of the inner blade 136 are longitudinally offset from the window teeth 176 of the outer blade 140. More particularly, tips 184 of the window teeth 176 of the cutting window 142 align with the valleys 158 between the teeth 150a, 150b of the cutting tip 138. The teeth 150a, 150b and the castellations 146a, 146b of the cutting tip 138 captures, or affixes, the tissue by locally piercing the target tissue in order to drag the tissue to the stationary window edges 172, 174, and 178 of the cutting window 142 so that a tissue bolus can be sheared free from the in situ fibrous tissue. The inwardly beveled edge surfaces of the cutting tip 138 and the outwardly beveled edge surfaces of the cutting window 142 create sharp shearing surfaces. In this manner, the rotating surface of the cutting tip 138 contacts the target tissue and drives the tissue into the stationary cutting window 142 surfaces to shear the tissue.

Minimal of deflection of the blades 136, 140 occurs, in one embodiment less than 0.008 inches, as the inner blade 136 and the associated cutting tip 138 are rotated in a single (i.e., non-oscillating) direction during the cutting procedure, providing stability to the cutting implement 122. The cutting tip 138 rotates as the target tissue is drawn toward the cutter 124 with the negative pressure such that the tissue contacts the cutting tip 138 and the tissue is cleanly and neatly cut (i.e., without tearing) against the edges of the cutting window 142 to minimize collateral damage to the surrounding tissue. The cutting tip 138 takes bites of tissue to effectively emulsify the targeted tissue. The fluid source 16 has been activated prior to rotation of the inner blade 136. The inner blade 136 is sized to accommodate the emulsified tissue, and thus, due to the small size of the tissue being removed through the inner blade 136", the inner blade 136 can be smaller than that of other debridders. Fluid from the fluid source assists with the emulsification and aspiration of the tumor. By controlling (minimizing) the aspiration at the cutting implement 122, unnecessary damage to the surrounding tissue is avoided. Additionally, due to the one-directional rotation of the cutting implement 122, the surgeon can precisely locate and maintain the cutting implement 122 at the desired tumor 400.

As discussed above, the irrigation path extends between the inner and outer blades 136, 140. The irrigation fluid then can exit the cutting window 142 to irrigate the target site. The irrigation fluid path provides constant irrigation of the target site and a liquid medium for material being cut and removed through the central lumen of the inner blade 136. The cutting window 142 and the lumen of the inner blade 136 serve as an aspiration outlet of the aspiration fluid pathway (FIG. 1) otherwise employed for aspirating a target site. Aspiration is manually controlled with the aspiration control hole 34 on the handpiece 20.

After removing the bulk of the tumor 400 using the cutting implement 122, the surgeon may remove the cutting implement 122 for the handpiece 20 and select and assemble the cutting implement 222 to the handpiece 20 to remove the remaining tumor 400 at the margins. The cutting implement 222 (or cutting implement 322) can provide smaller and more precise removal of the tumor. After use, in some embodiments, the cutting implement can be disassembled after disengagement from the handpiece 20 for cleaning or other purposes. For example, the inner blade 336 can be disassembled from the outer blade 340 for cleaning or repair.

Although specific examples have been illustrated and described herein, a variety of alternate and/or equivalent implementations may be substituted for the specific examples shown and described without departing from the scope of the present disclosure. This application is intended to cover any adaptations or variations of the specific examples discussed herein. Therefore, it is intended that this disclosure be limited only by the claims and the equivalents thereof.

What is claimed is:

1. A surgical method of removing tissue of a patient, comprising:

grasping a surgical cutting instrument, the instrument comprising:
an outer blade including a tubular body, an end cap, and a cutting window defined by an edge on at least the end cap, and
an inner blade co-axially disposed within the outer blade, the inner blade having tubular side walls and an open distal end formed at a distal end of the tubular side walls, the distal end positioned adjacent the end cap of the outer blade, the inner blade including a cutting tip having a first side wall opening including cutting teeth extending circumferentially toward one another across the first side wall opening and defining side surfaces of the first side wall opening, a second side wall opening circumferentially spaced from the first wall opening, and at least two projections longitudinally extending toward the open distal end between the first side wall opening and the second side wall opening, each of the at least two projections including an end cutting surface extending parallel to a plane of the end cap, wherein the open distal end is open between the at least two projections with the end cutting surface of each of the at least two projections independently and separately terminating at the open distal end, wherein the cutting tip is rotatably exposed at the cutting window;

positioning the cutting window and cutting tip to a target site;

supplying fluid through an irrigation pathway to the cutting window and the target site;

rotating the cutting tip of the inner blade to selectively cut the tissue; and aspirating fluid and cut tissue.

2. The method of claim 1, wherein the end cutting surfaces of the cutting tip directly contacts an inner surface of the end cap.

3. The method of claim 1, wherein rotating the cutting tip a single revolution exposes the tissue to at least three end cutting surfaces of the cutting tip.

4. The method of claim 1, wherein the irrigation pathway includes an irrigation channel recess in a distal portion of the inner blade, and wherein the irrigation channel recess terminates at the distal portion.

5. The method of claim 1, wherein the cutting teeth extending radially toward one another across the first side wall opening of the cutting tip.

6. The method of claim 5, wherein tips of the teeth of the cutting tip are offset from tips of teeth on the edge of the cutting window.

7. A surgical method of removing tissue of a patient, comprising:

operating a surgical system including a surgical instrument comprising:

an outer blade including a tubular body extending along a longitudinal axis and a planar distal end cap disposed perpendicular to the longitudinal axis, wherein a cutting window is at least partially formed in the distal end cap;

an inner blade including a cutting tip having an open distal end rotatably received within the outer blade, the cutting tip including a central opening defined by radial side edges and at least one second opening circumferentially spaced from the central opening along a tubular side wall, the central opening and the at least one second opening separated by projections, each projection including a freely terminating end defining an end cutting surface perpendicular to a tubular side wall of the inner blade and beveled along the tubular side wall at the open distal end, the central opening and the at least one second opening extending along the longitudinal axis from the open distal end of the cutting tip, the tubular side wall forming a cutting plane perpendicular to the longitudinal axis at the open distal end, the cutting tip selectively exposed at the cutting window;

an aspiration pathway defined by the inner blade; and an irrigation pathway defined between an outer surface of the inner blade and an inner surface of the outer blade, wherein the irrigation and aspiration pathways terminating at the cutting window;

delivering the surgical instrument to a target site;

positioning the cutting window and cutting tip at the target site;

supplying fluid through the irrigation pathway to the cutting tip;

selectively rotating the inner blade in a single direction;

emulsifying the tissue selectively exposed to the cutting tip; and selectively aspirating fluid and emulsified tissue through the cutting window and aspiration pathway.

8. The method of claim 7, wherein the surgical instrument further includes a handpiece for maintaining proximal ends of the inner and outer blades.

9. The method of claim 8, comprising:

biasing the cutting tip toward the distal end cap, wherein the biasing is effected within the handpiece.

10. The method of claim 7, comprising:

manually varying aspiration by sliding a finger over an aspiration control.

11. The method of claim 7, wherein the cutting window is formed on the outer blade adjacent to the distal end cap.

12. The method of claim 11, wherein the cutting tip includes end cutting edges configured for cutting at the cutting window formed at the planar distal end cap and side cutting edges configured for cutting at the cutting window formed on the outer blade.

13. The method of claim 7, comprising:

impaling tissue with the cutting tip during rotation.

14. The method of claim 13, comprising:

shearing the impaled tissue against a cutting window edge.

15. A surgical method of removing tissue of a patient, comprising:

operating a surgical cutting system, comprising:

a surgical cutting instrument including:

an outer blade, an inner blade coaxially received within an outer tubular member, a distal end of the inner blade and the outer blade forming a cutter including at least one cutting window on the outer tubular member and a cutting tip including radial cutting surfaces and an end cutting surface rotatable with the inner blade, and a handpiece including a manual aspiration control, the handpiece fixedly maintaining a proximal end of the outer blade and rotatably maintaining a proximal end of the inner blade;

fluidly coupling an irrigation source to a lumen of the outer blade;

fluidly coupling a negative pressure source to the inner blade;

selectively controlling the irrigation source with an electrical console;

delivering the cutting window and cutting tip to a target site;

supplying fluid through an irrigation pathway at least partially disposed between a proximal portion of the inner blade having a first outer diameter and the outer blade and through an irrigation channel recessed from a second outer diameter of a distal portion of the inner blade to the cutting window, the first outer diameter being smaller than the second outer diameter;

selectively controlling the rotation of the inner blade via the electrical console;

rotating the inner blade to selectively expose the cutting tip at the at least one cutting window, at least a portion of the end cutting surface selectively exposed at the at least one cutting window separately from the radial cutting surfaces;

emulsifying tissue exposed to the cutting tip; and aspirating the emulsified tissue and fluid via the negative pressure source.

16. The method of claim 15, comprising:
manually varying the aspiration with an aspiration control on the handpiece.

17. The method of claim 15, comprising:
impaling tissue with the cutting tip;
drawing the impaled tissue into the cutting window; and
shearing the impaled tissue at a cutting window edge during rotation of the inner blade.

18. The method of claim 15, comprising:
disassembling the inner blade from the outer blade.

* * * * *